(12) United States Patent
Kato et al.

(10) Patent No.: US 7,067,520 B2
(45) Date of Patent: Jun. 27, 2006

(54) PREVENTIVE OR THERAPEUTIC MEDICINES FOR DIABETES CONTAINING FUSED-HETEROCYCLIC COMPOUNDS OR THEIR SALTS

(75) Inventors: Fuminori Kato, Shiga (JP); Hirohiko Kimura, Shiga (JP); Masato Omatsu, Shiga (JP); Kazuhiro Yamamoto, Shiga (JP); Ryuji Miyamoto, Shiga (JP)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 312 days.

(21) Appl. No.: 10/416,164

(22) PCT Filed: Nov. 15, 2001

(86) PCT No.: PCT/JP01/10061

§ 371 (c)(1),
(2), (4) Date: May 15, 2003

(87) PCT Pub. No.: WO02/40485

PCT Pub. Date: May 23, 2002

(65) Prior Publication Data

US 2004/0043998 A1    Mar. 4, 2004

(30) Foreign Application Priority Data

Nov. 16, 2000    (JP) .............................. 2000-351764

(51) Int. Cl.
| | |
|---|---|
| C07D 487/04 | (2006.01) |
| A61K 31/519 | (2006.01) |
| A61P 3/10 | (2006.01) |
| A61P 3/06 | (2006.01) |
| A61P 9/00 | (2006.01) |

(52) U.S. Cl. .................................. 514/259.3; 544/263
(58) Field of Classification Search ................ 544/250, 544/251, 252, 254, 256, 262, 281, 263; 514/259.1, 514/259.3, 259.31, 264.1
See application file for complete search history.

(56) References Cited

U.S. PATENT DOCUMENTS 3,202,512 A  *  8/1965  Leslie ......................... 430/611
5,902,773 A  *  5/1999  Benoit et al. ................. 504/240

FOREIGN PATENT DOCUMENTS

| DE | 255734 A1 | * | 4/1988 |
| JP | 37005946 | * | 6/1962 |
| JP | 402671 B4 | * | 1/1965 |
| JP | 40005840 | * | 3/1965 |
| JP | 07168303 | * | 7/1995 |
| JP | 2001302666 | * | 10/2001 |
| NL | 6501053 | * | 7/1965 |
| WO | 98/54093 | | 12/1998 |
| WO | 00/44754 | | 8/2000 |

OTHER PUBLICATIONS

Zaharan et al. Farmaco 56(4): 277-283, 2001.*
Hori et al. Bulletin of the Chemical Society of Japan 43(3), 849-855, 1970.*
Tominaga et al. Chemical & Pharmaceutical Bulletin 33(3), 962-970.*
Hempel et al. Zeitschrift fuer Chemie 30(5) 170-175 1990.*
Mohamed et al. Archiv der Pharmazie 326(4): 245-270, 1993.*
Elgemeie et al. phosphorus, Sulfur and Silicon and the Related Elements 90(1-4) 143-146, 1994. 33(3), 962-970.*
Ram et al. Indian Journal of Chemistry Section B 34B(5) 416-422, 1995.*
Reiter et al. Journal of Heterocyclic Chemistry 32(2) 407-417, 1995.*
Hasan et al. Pharmazie 52(8) 589-593, 1997.*
Obrosova et al., Diabetologia, 42(10): 1187-1194,1999.*

(Continued)

*Primary Examiner*—Venkataraman Balasubramanian
(74) *Attorney, Agent, or Firm*—Oblon, Spivak, McClelland, Maier & Neustadt, P.C.

(57) ABSTRACT

The present invention provides a preventive or therapeutic medicine for diabetes containing as an active ingredient a fused-heterocyclic compound of the formula (I') or its salt:

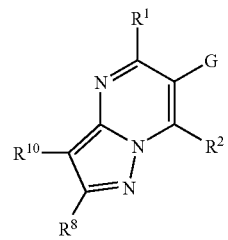

[wherein G is CN, $NO_2$, $CO_2R^4$, CHO, $SO_2NR^aR^b$ or $CONR^aR^b$; $R^1$ is a halogen atom, a —O—$R^5$ group or a —S—$R^5$ group; $R^2$ is a halogen atom, a —O—$R^5$ group (wherein $R^5$ is as defined above) or an amino group which may be substituted; and each of $R^8$ and $R^{10}$ which are independent of each other, is a hydrogen atom, a halogen atom or an alkyl group].

10 Claims, No Drawings

OTHER PUBLICATIONS

Yoshinori Tominaga et al.: "Synthesis of polycyclic nitrogen-containing heterocycles: one pot formation of 1,6-naphthyridine ring system by reaction of amino- cyano-methylthio-heterocycles with dialkyl acetylenedicarboxylates" Hetercycles, vol. 42, No. 1, pp. 53-56, 1996.

* cited by examiner

PREVENTIVE OR THERAPEUTIC MEDICINES FOR DIABETES CONTAINING FUSED-HETEROCYCLIC COMPOUNDS OR THEIR SALTS

TECHNICAL FIELD

The present invention relates to preventive or therapeutic medicines for diabetes, which contain specific fused-heterocyclic compounds or their salts as active ingredients. Further, some of fused-heterocyclic compounds or their salts as described hereinafter are novel substances. The preventive or therapeutic medicines for diabetes of the present invention have a stimulating effect on glucose uptake and a hypoglycemic effect, and they are useful as preventive or therapeutic medicines for diabetes; impaired glucose tolerance; various diabetic complications such as hyperlipidemia, vascular diseases, retinopathy, nephropathy, neuropathy and hypertension; and obesity.

BACKGROUND ART

As general antidiabetic agents having a hypoglycemic effect, insulin preparations and oral hypoglycemic agents are mainly utilized. The oral hypoglycemic agents may, for example, be islet-activating agents represented by sulfonylurea agents, liver gluconeogenesis inhibitors represented by biguanides and insulin sensitizers represented by thiazolidine derivatives. However, these therapeutic medicines are not effectively affect on many patients, and it is not easy to control the blood glucose level only by these therapeutic medicines, and various diabetic complications are caused in fact. Among peripheral organs in the body, a muscle is the most important tissue which plays a role of glucose metabolism at the time of hyperglycemia, and a decrease in glucose uptake activity of skeletal muscle cells is considered to be one of great factors causing hyperglycemia to diabetic patients. Therapeutic medicines for diabetes which directly accelerate glucose uptake activity in skeletal muscles as a principal action without depending on insulin are hypoglycemic agents of new types, and therapeutic medicines as disclosed in JP-A-6-345647 and JP-A-8-12579 have been proposed, but have not been used practically yet. These patent applications disclose that it takes so long time of 24 hours to apply a compound under test to skeletal muscle cells, and do not disclose the effect in a case of application for a level of 1 hour. The present inventors have found that a stimulating effect on glucose uptake is obtained by applying compounds of the formula (I) as described hereinafter having structures totally different from those in the above patent applications to skeletal muscle cells for a short time. Further, they have also confirmed that the compounds of the formula (I) as described hereinafter show a hypoglycemic effect or an effect of improving impaired glucose tolerance, several hours after administration of the compounds to diabetic KK-Ay mice and the like.

As compounds having chemical structures analogous to those of the compounds of the formula (I) as described hereinafter, compounds as disclosed in WO97/35550, WO99/60858 and WO00/44754 may be mentioned. However, these patent applications fail to disclose the effect as stimulators of glucose uptake in skeletal muscle cells.

DISCLOSURE OF THE INVENTION

The present inventors have found that when a specific fused-heterocyclic compound or its salt is applied to skeletal muscle cells for a short time, a stimulating effect on glucose uptake is obtained, and the present invention has been accomplished on the basis of this discovery.

The present inventors have conducted extensive studies to find more excellent antidiabetic agents and as a results, have accomplished the present invention. Namely, the present invention relates to a preventive or therapeutic medicine for diabetes containing as an active ingredient a fused-heterocyclic compound of the formula (I) or its salt:

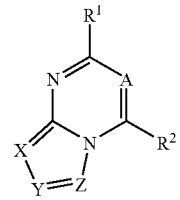

[wherein A is a nitrogen atom or C-G {wherein G is CN, $NO_2$, $SO_2R^3$ (wherein $R^3$ is an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted), $CO_2R^4$ (wherein $R^4$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted), CHO, $SO_2NR^aR^b$ (wherein each of $R^a$ and $R^b$ which are independent of each other, is a hydrogen atom, a hydroxyl group, an alkoxy group, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted, or $R^a$ and $R^b$ together form a ring) or $CONR^aR^b$ (wherein $R^a$ and $R^b$ are as defined above)};

each of $R^1$ and $R^2$ which are independent of each other, is a hydrogen atom, a halogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, a —$B^1$—$R^5$ group (wherein $B^1$ is CO, COO, O, OCO, $OSO_2$, S, SO or $SO_2$, and $R^5$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted), an amino group which may be substituted or —N=$CR^6R^7$ (wherein each of $R^6$ and $R^7$ which are independent of each other, is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted);

each of Y and Z which are independent of each other, is a nitrogen atom or C—R$^8$ (wherein R$^8$ is a hydrogen atom, a halogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, a —B$^2$—R$^9$ group (wherein B$^2$ is CO, COO, O, OCO, OSO$_2$, S, SO or SO$_2$, and R$^9$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted), an amino group which may be substituted, a cyano group or a nitro group), provided that when Y and Z are simultaneously C—R$^8$, the two R$^8$'s may be the same or different;

X is a nitrogen atom or C—R$^{10}$ (wherein R$^{10}$ is a hydrogen atom, a halogen atom, an alkyl group which may be substituted, an alkenyl group which may be substituted, an alkynyl group which may be substituted, a cycloalkyl group which may be substituted, a cycloalkenyl group which may be substituted, a —B$^2$—R$^9$ group (wherein B$^2$ and R$^9$ are as defined above), an amino group which may be substituted, a cyano group or a nitro group); and in a case where Y is C—R$^8$, and X is C—R$^{10}$ or Z is C—R$^8$, R$^8$ and R$^{10}$ or two R$^8$'s together may form a ring containing or not containing a hetero atom].

The salt of the fused-heterocyclic compound of the above formula (I) may be any pharmaceutically acceptable salt, and it may, for example, be a mineral acid salt such as a hydrochloride, a sulfate or a nitrate; an organic acid salt such as a p-toluenesulfonate, a propane sulfonate or a methane sulfonate; an alkali metal salt such as a potassium salt or a sodium salt; an alkaline earth metal salt such as a calcium salt; or an organic amine salt such as a triethanol amine salt or a tris(hydroxymethyl) aminomethane salt. Some of these salts have crystal water.

The alkyl moiety of the alkyl group which may be substituted represented by each of R$^1$, R$^2$, R$^3$, R$^4$, R$^5$, R$^6$, R$^7$, R$^8$, R$^9$, R$^{10}$, R$^a$ and R$^b$ in the formula (I) may be usually one having a carbon number of from 1 to 18, and it may, for example, be a methyl group, an ethyl group, a propyl group, a butyl group, a pentyl group, a hexyl group, an octyl group, a nonyl group, a decyl group or a nonadecyl group, and they include linear or branched aliphatic structural isomers.

The alkenyl moiety of the alkenyl group which may be substituted or the alkynyl moiety of the alkynyl group which may be substituted, represented by each of R$^1$, R$^2$, R$^3$, R$^4$, R$^5$, R$^6$, R$^7$, R$^8$, R$^9$, R$^{10}$, R$^a$ and R$^b$ in the formula (I), may be usually one having a carbon number of from 2 to 18, and they include linear or branched aliphatic structural isomers.

The cycloalkyl moiety of the cycloalkyl group which may be substituted or the cycloalkenyl moiety of the cycloalkenyl group which may be substituted, represented by each of R$^1$, R$^2$, R$^3$, R$^4$, R$^5$, R$^6$, R$^7$, R$^8$, R$^9$, R$^{10}$, R$^a$ and R$^b$ in the formula (I), may be usually one having a carbon number of from 3 to 10, and it may, for example, be a monocyclic group such as a cyclopropyl group, a cyclobutyl group, a cyclopentyl group, a cyclohexyl group, a cyclopentenyl group or a cyclohexenyl group, a fused-polycyclic group or a crosslinked polycyclic group.

The aryl moiety of the aryl group which may be substituted represented by each of R$^1$, R$^2$, R$^3$, R$^4$, R$^5$, R$^6$, R$^7$, R$^8$, R$^9$, R$^a$ and R$^b$ in the formula (I) may be a fused-polycyclic group such as a naphthyl group, as well as a phenyl group.

The heterocyclic moiety of the heterocyclic group which may be substituted represented by each of R$^1$, R$^2$, R$^3$, R$^4$, R$^5$, R$^6$, R$^7$, R$^8$, R$^9$, R$^a$ and R$^b$ in the formula (I), may, for example, be a monocyclic heterocyclic group such as a pyrrolyl group, a pyrrolinyl group, a pyrrolidinyl group, a furanyl group, a dihydrofuranyl group, a tetrahydrofuranyl group, a thienyl group, a dihydrothienyl group, a tetrahydrothienyl group, a pyrazolyl group, a pyrazolinyl group, a pyrazolidinyl group, an imidazolyl group, an imidazolinyl group, an imidazolidinyl group, an oxazolyl group, an oxazolinyl group, an oxazolidinyl group, an isoxazolyl group, an isoxazolinyl group, an isoxazolidinyl group, a thiazolyl group, a thiazolinyl group, a thiazolidinyl group, an isothiazolyl group, an isothiazolinyl group, an isothiazolidinyl group, an oxadiazolyl group, an oxadiazolinyl group, an oxadiazolidinyl group, a thiadiazolyl group, a thiadiazolinyl group, a thiadiazolidinyl group, a triazolyl group, a triazolinyl group, a triazolidinyl group, a tetrazolyl group, a tetrazolinyl group, a tetrazolidinyl group, a dioxolyl group, a dioxolanyl group, a dithiolyl group, a dithiolanyl group, a pyridyl group, a dihydropyridyl group, a tetrahydropyridyl group, a piperidinyl group, a pyrimidyl group, a dihydropyrimidyl group, a tetrahydropyrimidyl group, a hexahydropyrimidyl group, a pyridazinyl group, a dihydropyridazinyl group, a tetrahydropyridazinyl group, a hexahydropyridazinyl group, a pyrazinyl group, a dihydropyrazinyl group, a tertahydropyrazinyl group, a piperazinyl group, a pyranyl group, a dihydropyranyl group, a tetrahydropyranyl group, a dioxinyl group, a dioxenyl group, a dioxanyl group, a dithianyl group or a morpholinyl group; a fused-polycyclic heterocyclic group such as a thienothienyl group, a dihydrocyclopentathienyl group, an indolyl group, a tetrahydroindolyl group, an isoindolyl group, a tetrahydroisoindolyl group, a benzothienyl group, a tetrahydrobenzothienyl group, a benzofuranyl group, a tetrahydrobenzofuranyl group, a benzoxazolyl group, a tetrahydrobenzoxazolyl group, a benzoisoxazolyl group, a tetrahydrobenzoisoxazolyl group, a benzothiazolyl group, a tetrahydrobenzothiazolyl group, a benzoisothiazolyl group, a tetrahydrobenzoisothiazolyl group, a benzoimidazolyl group, a tetrahydrobenzimidazolyl group, a benzodioxolyl group, a benzodithiolyl group, a benzodioxanyl group, a benzodithianyl group, a quinolinyl group, an isoquinolinyl group, a quinazolinyl group, a quinoxalinyl group, a phthalazinyl group, a naphthylidinyl group or a purinyl group; or a crosslinked polycyclic heterocyclic group such as a quinuclidinyl group.

The secondary substituent of each of the alkyl group which may be substituted, the alkenyl group which may be substituted and the alkynyl group which may be substituted, represented by each of R$^1$, R$^2$, R$^3$, R$^4$, R$^5$, R$^6$, R$^7$, R$^8$, R$^9$, R$^{10}$, R$^a$ and R$^b$ in the formula (I), may, for example, be a halogen atom, a hydroxyl group, a mercapto group, a substitutable alkoxy group, a substitutable alkylthio group, a substitutable alkenyloxy group, a substitutable alkenylthio group, a substitutable alkynyloxy group, a substitutable alkynylthio group, a substitutable cycloalkyl group, a substitutable cycloalkenyl group, a substitutable cycloalkoxy group, a substitutable cycloalkylthio group, a substitutable cycloalkenyloxy group, a substitutable cycloalkenylthio group, a substitutable alkoxycarbonyl group, a substitutable alkylcarbonyl group, a substitutable alkylcarbonyloxy group, a substitutable alkenyloxycarbonyl group, a substitutable alkenylcarbonyl group, a substitutable alkenylcarbonyloxy group, a substitutable alkynyloxycarbonyl group, a substitutable alkynylcarbonyl group, a substitutable alkynylcarbonyloxy group, a substitutable cycloalkoxycarbonyl group, a substitutable cycloalkylcarbonyl group, a substitutable cycloalkylcarbonyloxy group, a substitutable cycloalkenyloxycarbonyl group, a substitutable cycloalkenylcarbonyl group, a substitutable cycloalkenylcarbonyloxy group, a substitutable aryl group, a substitutable aryloxy group, a substitutable arylthio group, a substitutable aryloxycarbonyl group, a substitutable arylcarbonyl group, a substitutable arylcarbonyloxy group, a substitutable heterocyclic group, a substitutable heterocyclyloxy group, a substitutable heterocyclylthio group, a substitutable heterocyclyloxycarbonyl group, a substitutable heterocyclylcarbonyl group, a substitutable heterocyclylcarbonyloxy group, a substitutable amino group, a cyano group, a nitro group, a carboxyl group, a substitutable aminocarbonyl group, a substitutable alkylsulfonyl group, a substitutable alkenylsulfonyl group, a substitutable alkynylsulfonyl group, a substitutable cycloalkylsulfonyl group, a substitutable cycloalkenylsulfonyl group, a substitutable arylsulfonyl group, a substitutable heterocyclylsulfonyl group or a substitutable aminosulfonyl group. The number of such substituents may be one or two or more, and when the number of the substituents is two or more, such substituents may be the same or different.

The secondary substituent of each of the cycloalkyl group which may be substituted, the cycloalkenyl group which may be substituted, the aryl group which may be substituted and the heterocyclic group which may be substituted, represented by each of $R^1$, $R^2$, $R^3$, $R^4$, $R^5$, $R^6$, $R^7$, $R^8$, $R^9$, $R^{10}$, $R^a$ and $R^b$ in the formula (I), may, for example, be a halogen atom, a hydroxyl group, a mercapto group, a substitutable alkyl group, a substitutable alkenyl group, a substitutable alkynyl group, a substitutable alkoxy group, a substitutable alkylthio group, a substitutable alkenyloxy group, a substitutable alkenylthio group, a substitutable alkynyloxy group, a substitutable alkynylthio group, a substitutable cycloalkyl group, a substitutable cycloalkenyl group, a substitutable cycloalkoxy group, a substitutable cycloalkylthio group, a substitutable cycloalkenyloxy group, a substitutable cycloalkenylthio group, a substitutable alkoxycarbonyl group, a substitutable alkylcarbonyl group, a substitutable alkylcarbonyloxy group, a substitutable alkenyloxycarbonyl group, a substitutable alkenylcarbonyl group, a substitutable alkenylcarbonyloxy group, a substitutable alkynyloxycarbonyl group, a substitutable alkynylcarbonyl group, a substitutable alkynylcarbonyloxy group, a substitutable cycloalkoxycarbonyl group, a substitutable cycloalkylcarbonyl group, a substitutable cycloalkylcarbonyloxy group, a substitutable cycloalkenyloxycarbonyl group, a substitutable cycloalkenylcarbonyl group, a substitutable cycloalkenylcarbonyloxy group, a substitutable aryl group, a substitutable aryloxy group, a substitutable arylthio group, a substitutable aryloxycarbonyl group, a substitutable arylcarbonyl group, a substitutable arylcarbonyloxy group, a substitutable heterocyclic group, a substitutable heterocyclyloxy group, a substitutable heterocyclylthio group, a substitutable heterocyclyloxycarbonyl group, a substitutable heterocyclylcarbonyl group, a substitutable heterocyclylcarbonyloxy group, a substitutable amino group, a cyano group, a nitro group, a carboxyl group, a substitutable aminocarbonyl group, a substitutable alkylsulfonyl group, a substitutable alkenylsulfonyl group, a substitutable alkynylsulfonyl group, a substitutable cycloalkylsulfonyl group, a substitutable cycloalkenylsulfonyl group, a substitutable arylsulfonyl group, a substitutable heterocyclylsulfonyl group or a substitutable aminosulfonyl group. The number of such substituents may be one or two or more, and when the number of the substituents is two or more, such substituents may be the same or different.

The secondary substituent of the amino group which may be substituted represented by each of $R^1$, $R^2$, $R^8$ and $R^{10}$ in the formula (I), may, for example, be a hydroxyl group, a substitutable alkyl group, a substitutable alkenyl group, a substitutable alkynyl group, a substitutable alkoxy group, a substitutable alkenyloxy group, a substitutable alkynyloxy group, a substitutable cycloalkyl group, a substitutable cycloalkenyl group, a substitutable cycloalkoxy group, a substitutable cycloalkenyloxy group, a substitutable alkoxycarbonyl group, a substitutable alkylcarbonyl group, a substitutable alkenyloxycarbonyl group, a substitutable alkenylcarbonyl group, a substitutable alkynyloxycarbonyl group, a substitutable alkynylcarbonyl group, a substitutable cycloalkoxycarbonyl group, a substitutable cycloalkylcarbonyl group, a substitutable cycloalkenyloxycarbonyl group, a substitutable cycloalkenylcarbonyl group, a substitutable aryl group, a substitutable aryloxy group, a substitutable aryloxycarbonyl group, a substitutable arylcarbonyl group, a substitutable heterocyclic group, a substitutable heterocyclyloxy group, a substitutable heterocyclyloxycarbonyl group, a substitutable heterocyclylcarbonyl group, a substitutable aminocarbonyl group, a substitutable alkylsulfonyl group, a substitutable alkenylsulfonyl group, a substitutable alkynylsulfonyl group, a substitutable cycloalkylsulfonyl group, a substitutable cycloalkenylsulfonyl group, a substitutable arylsulfonyl group, a substitutable heterocyclylsulfonyl group or a substitutable aminosulfonyl group. The number of such secondary substituents may be one or two, and when the number is two, they may be the same or different. Further, the two secondary substituents may form a ring containing or not containing a hetero atom.

The tertiary substituent of each of substitutable groups among the above secondary substituents may, for example, be a halogen atom, a hydroxyl group, a mercapto group, a cyano group, a nitro group, a carboxyl group, an amino group, an alkyl group, an alkenyl group, an alkynyl group, a cycloalkyl group, a cycloalkenyl group, an aryl group, a heterocyclic group, an alkoxy group, an alkenyloxy group, an alkynyloxy group, a cycloalkyloxy group, a cycloalkenyloxy group, an aryloxy group, a heterocyclyloxy group, an alkylthio group, an alkenylthio group, an alkynylthio group, a cycloalkylthio group, a cycloalkenylthio group, an arylthio group, a heterocyclylthio group, an alkylsulfonyl group, an alkenylsulfonyl group, an alkynylsulfonyl group, a cycloalkylsulfonyl group, a cycloalkenylsulfonyl group, an arylsulfonyl group, a heterocyclylsulfonyl group, an alkylcarbonyl group, an alkenylcarbonyl group, an alkynylcarbonyl group, a cycloalkylcarbonyl group, a cycloalkenylcarbonyl group, an arylcarbonyl group, a heterocyclylcarbonyl group, an alkyloxycarbonyl group, an alkenyloxycarbonyl group, an alkynyloxycarbonyl group, a cycloalkyloxycarbonyl group, a cycloalkenyloxycarbonyl group, an aryloxycarbonyl group, a heterocyclyloxycarbonyl group, an aminocarbonyl group, an alkylaminocarbonyl group, a dialkylaminocarbonyl group, an alkenylaminocarbonyl group, an alkynylaminocarbonyl group, a cycloalkylaminocarbonyl group, a cycloalkenylaminocarbonyl group, an arylaminocarbonyl group, a heterocyclylaminocarbonyl group, an aminosulfonyl group, an alkylaminosulfonyl group, a dialkylaminosulfonyl group, an alkenylaminosulfonyl group, an alkynylaminosulfonyl group, a cycloalkylaminosulfonyl group, a cycloalkenylaminosulfonyl group, an arylaminosulfonyl group, a heterocyclylaminosulfonyl group, an alkylamino group, a dialkylamino group, an alkenylamino group, an alkynylamino group, a cycloalkylamino group, a cycloalkenylamino group, an arylamino group, a heterocyclylamino group, an alkylcarbonylamino group, an alkenylcarbonylamino group, an alkynylcarbonylamino group, a cycloalkylcarbonylamino group, a cycloalkenylcarbonylamino group, an arylcarbonylamino group, a heterocyclylcarbonylamino group, an alkylsulfonylamino group, an alkenylsulfonylamino group, an alkynylsulfonylamino group, a cycloalkylsulfonylamino group, a cycloalkenylsulfonylamino group, an arylsulfonylamino group or a heterocyclylsulfonylamino group. The number of such tertiary substituents may be one or two or more, and when the number is two or more, such substituents may be the same or different. Further, when the secondary substituent is an amino group substituted with two tertiary substituents, such tertiary substituents together may form a ring containing or not containing a hetero atom.

Further, each of the alkyl moiety, the alkenyl moiety, the alkynyl moiety, the cycloalkyl moiety, the cycloalkenyl moiety, the aryl moiety and the heterocyclic moiety of each of such tertiary substituents may further be substituted with a quaternary substituent such as a halogen atom, a hydroxyl group, a mercapto group, a cyano group, a nitro group, a carboxyl group, an amino group, an alkyl group, a haloalkyl group, an alkoxy group, a haloalkoxy group, an alkylthio group, a haloalkylthio group, an alkoxycarbonyl group, an aminocarbonyl group, an alkylaminocarbonyl group, a dialkylaminocarbonyl group, an aminosulfonyl group, an alkylaminosulfonyl group, a dialkylaminosulfonyl group, an alkylamino group, a dialkylamino group, an alkylcarbonylamino group, an alkylsulfonylamino group, a cycloalkyl group, an aryl group or a heterocyclic group. The number of such substituents may be one or two or more, and when the number of the substituents is two or more, such substituents may be the same or different.

Among the fused-heterocyclic compounds of the above formula (I) and their salts, fused-heterocyclic compounds of the formula (I') and their salts:

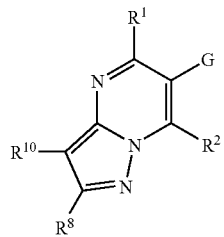

[wherein G is CN, NO$_2$, CO$_2$R$^4$ (wherein R$^4$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted), CHO, SO$_2$NR$^a$R$^b$ (wherein each of R$^a$ and R$^b$ which are independent of each other, is a hydrogen atom, a hydroxyl group, an alkoxy group, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted, or R$^a$ and R$^b$ together form a ring) or CONR$^a$R$^b$ (wherein R$^a$ and R$^b$ are as defined above);

R$^1$ is a halogen atom, a —O—R$^5$ group (wherein R$^5$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted) or a —S—R$^5$ group (wherein R$^5$ is as defined above);

R$^2$ is a halogen atom, a —O—R$^5$ group (wherein R$^5$ is as defined above) or an amino group which may be substituted; and each of R$^8$ and R$^{10}$ which are independent of each other, is a hydrogen atom, a halogen atom or an alkyl group], are novel compounds.

BEST MODE FOR CARRYING OUT THE INVENTION

Now, some of preferred embodiments of the present invention will be explained, however, the present invention is by no means restricted thereto.

The compounds of the above formula (I) and the compounds of the formula (I') included therein, are useful as active ingredients for preventive or therapeutic medicines for diabetes, and are useful as the following agents for example.

(1) Stimulators of glucose uptake in skeletal muscle cells.
(2) Hypoglycemic agents.
(3) Preventive or therapeutic medicines for impaired glucose tolerance.
(4) Preventive or therapeutic medicines for diabetic complications.
(5) Preventive or therapeutic medicines for at least one diabetic complication selected from the group consisting of hyperlipidemia, vascular diseases, retinopathy, nephropathy, neuropathy and hypertension.
(6) Preventive or therapeutic medicines for obesity.

Among the compounds of the above formula (I), the following compounds are excellent as active ingredients for preventive or therapeutic medicines for diabetes.

(1) Compounds wherein A is C-G {wherein G is CN, NO$_2$, CO$_2$R$^4$ (wherein R$^4$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted), CHO, SO$_2$NR$^a$R$^b$ (wherein each of R$^a$ and R$^b$ which are independent of each other, is a hydrogen atom, a hydroxyl group, an alkoxy group, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted, or R$^a$ and R$^b$ together form a ring) or CONR$^a$R$^b$ (wherein R$^a$ and R$^b$ are as defined above)};

each of Y and Z which are independent of each other, is a nitrogen atom or C—R$^8$ {wherein R$^8$ is a hydrogen atom, a halogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, a —B$^2$—R$^9$ group (wherein B$^2$ is CO, COO, O, OCO, OSO$_2$, S, SO or SO$_2$, and R$^9$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted), an amino group which may be substituted, a cyano group or a nitro group}, provided that when Y and Z are simultaneously C—$R^8$, the two $R^8$'s may be the same or different; and X is a nitrogen atom or C—$R^{10}$ {wherein $R^{10}$ is a hydrogen atom, a halogen atom, an alkyl group which may be substituted, an alkenyl group which may be substituted, an alkynyl group which may be substituted, a cycloalkyl group which may be substituted, a cycloalkenyl group which may be substituted, a —$B^2$—$R^9$ group (wherein $B^2$ and $R^9$ are as defined above), an amino group which may be substituted, a cyano group or a nitro group}.

(2) Compounds wherein each of $R^1$ and $R^2$ which are independent of each other, is a halogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, a —$B^{1'}$—$R^5$ group (wherein $B^{1'}$ is O or S, and $R^5$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted), an amino group which may be substituted or —N=$CR^6R^7$ (wherein each of $R^6$ and $R^7$ which are independent of each other, is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted); and each of Y and Z which are independent of each other, is a nitrogen atom or C—$R^8$ {wherein $R^8$ is a hydrogen atom, a halogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, a —$B^{2'}$—$R^9$ group (wherein $B^{2'}$ is CO, COO, O, OCO or S, and $R^9$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted), an amino group which may be substituted, a cyano group or a nitro group).

Among the compounds of the above formula (I), the compounds of the above formula (I') are more excellent as active ingredients for preventive or therapeutic medicines for diabetes. No pharmaceutical compositions containing the compound of the formula (I') have conventionally been known. Among the compounds of the formula (I'), more preferred compounds are mentioned below.

(i) Compounds of the formula (I') wherein $R^2$ is an amino group which may be substituted.

(ii) Compounds of the formula (I') wherein $R^2$ is an amino group which may be substituted, and each of $R^8$ and $R^{10}$ is a hydrogen atom.

(iii) Compounds of (ii) wherein the amino group which may be substituted represented by $R^2$ is a —$NR^cR^d$ group {wherein each of $R^c$ and $R^d$ which are independent of each other, is a hydrogen atom, a —O—$R^5$ group (wherein $R^5$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted), an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted, or $R^c$ and $R^d$ together form a ring}.

(iv) Compounds of the formula (I') wherein G is CN, $CO_2R^4$ (wherein $R^4$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted), CHO, $SO_2NR^aR^b$ (wherein each of $R^a$ and $R^b$ which are independent of each other, is a hydrogen atom, a hydroxyl group, an alkoxy group, an alkyl group which may be substituted, an alkenyl group which may be substituted, an alkynyl group which may be substituted, a cycloalkyl group which may be substituted, a cycloalkenyl group which may be substituted or a heterocyclic group which may be substituted, or $R^a$ and $R^b$ together form a ring) or $CONR^{a'}R^{b'}$ (wherein each of $R^{a'}$ and $R^{b'}$ which are independent of each other, is a hydroxyl group, an alkoxy group, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted, or $R^{a'}$ and $R^{b'}$ together form a ring).

(v) Compounds of the formula (I') wherein G is CN, $NO_2$, $CO_2R^4$ (wherein $R^4$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted), CHO, C—$SO_2NR^aR^b$ (wherein each of $R^a$ and $R^b$ which are independent of each other, is a hydrogen atom, a hydroxyl group, an alkoxy group, an alkyl group which may be substituted, an alkenyl group which may be substituted, an alkynyl group which may be substituted, a cycloalkyl group which may be substituted, a cycloalkenyl group which may be substituted or a heterocyclic group which may be substituted, or $R^a$ and $R^b$ together form a ring) or $CONR^{a'}R^{b'}$ (wherein each of $R^{a'}$ and $R^{b'}$ which are independent of each other, is a hydroxyl group, an alkoxy group, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted, or $R^{a'}$ and $R^{b'}$ together form a ring); and $R^1$ is a —O—$R^5$ group (wherein $R^5$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted) or a —S—$R^5$ group ($R^5$ is an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted).

Each of the alkyl group which may be substituted, the alkenyl group which may be substituted, the alkynyl group which may be substituted, the cycloalkyl group which may be substituted, the cycloalkenyl group which may be substituted, the aryl group which may be substituted and the heterocyclic group which may be substituted in each of the substituents represented by each of $R^c$ and $R^d$ in the —$NR^c$ $R^d$ group in the above formula (iii) is as defined for each of the substituents in the compound of the formula (I). Further, as the —$NR^cR^d$ group, a substitutable alkylamino group, a substitutable dialkylamino group, an alkylcarbonylamino group, a substitutable alkynylamino group, a cycloalkylamino group or a substitutable arylamino group is preferred, and a substitutable alkylamino group or a substitutable arylamino group is more preferred. The substitutable alkylamino group may, for example, be a benzylamino group, a 4-nitrobenzylamino group, a 4-pyridylmethylamino group, a 3-pyridylmethylamino group, a 2-pyridylmethylamino group, a dioxolanylmethylamino group, a pyranylmethylamino group, a methylamino group, an ethylamino group or a dimethylamino group. The substitutable arylamino group may, for example, be a phenylamino group, a 4-cyanophenylamino group, a 3-cyanophenylamino group, a 4-chlorophenylamino group, a 2-chlorophenylamino group, a 4-methylphenylamino group, a 3-methylphenylamino group, a 2-methylphenylamino group, a 4-nitrophenylamino group or a 3-nitrophenylamino group.

The preventive or therapeutic medicines for diabetes of the present invention are usually used in the form of a common pharmaceutical preparation. The pharmaceutical preparation is prepared by using a commonly used diluent or excipient such as a bulking agent, an extender, a binding agent, a moisture-imparting agent, a disintegrator, a surfactant or a lubricant. As the pharmaceutical preparation, various forms may be selected depending upon the purpose of treatment, and a tablet, a pill, a powder, a dust, a granule, a capsule, a suppository, a solution, a suspension, an emulsion, an injection (such as a solution or a suspension), a spray, an aerosol, a cream, an ointment, a lotion or a transdermal agent (a patch, a matrix or a tape) may be mentioned as examples.

To form the medicine into a tablet, carriers which have conventionally been known in this field can be used widely, and they may, for example, be excipients such as lactose, sucrose, sodium chloride, glucose, urea, starch, calcium carbonate, kaolin, crystalline cellulose and silicic acid, binding agents such as water, ethanol, propanol, simple syrup, a glucose solution, a starch solution, a gelatin solution, carboxymethyl cellulose, Shellac, methyl cellulose, potassium phosphate and polyvinyl pyrrolidone, disintegrators such as dried starch, sodium alginate, an agar powder, a laminaran powder, sodium hydrogencarbonate, calcium carbonate, polyoxyethylene sorbitan fatty acid esters, sodium lauryl sulfate, monoglyceryl stearate, starch and lactose, disintegration inhibitors such as sucrose, stearin, cacao butter and hydrogenated oil, absorption stimulators such as a quaternary ammonium base and sodium lauryl sulfate, moisturizers such as glycerin and starch, absorbents such as starch, lactose, kaolin, bentonite and colloidal silicate, and lubricants such as purified talc, a stearate, a boric acid powder and polyethylene glycol. Further, a tablet may be a tablet having a common coating applied thereto as the case requires, such as a sugar-coated tablet, a gelatin-coated tablet, an enteric-coated tablet or a film-coated tablet, or a double tablet or a multilayer tablet.

To form the medicine into a pill, carriers which have conventionally been known in this field can be used widely, and they may, for example, be excipients such as glucose, lactose, starch, cacao butter, hydrogenated vegetable oil, kaolin and talc, binding agents such as powdered acacia, powdered tragacanth, gelatin and ethanol and disintegrators such as laminaran agar.

To form the medicine into a suppository, conventionally known carriers can be used widely, and they may, for example, be polyethylene glycol, cacao butter, higher alcohols, higher alcohol esters, gelatin and semi-synthetic glyceride.

To prepare an injection, a solution, an emulsion or a suspension is sterilized, and is preferably isotonic with the blood, and to form the medicine into a solution, an emulsion or a suspension, all the diluents which are commonly used in this field can be used, and they may, for example, be water, a lactic acid aqueous solution, ethyl alcohol, propylene glycol, ethoxylated isostearyl alcohol, polyoxylated isostearyl alcohol and polyoxyethylene sorbitan fatty acid esters. In this case, salt, glucose or glycerin in an amount adequate to prepare an isotonic solution may be incorporated in the pharmaceutical preparation, and a common solubilizing agent, buffer, soothing agent or the like may be added thereto. Further, as the case requires, a colorant, a preservative, a fragrant material, a flavoring agent, a sweetener or another pharmaceutical agent may be incorporated in the pharmaceutical preparation.

The amount of the compound of the above formula (I) to be contained in the therapeutic medicine for diabetes of the present invention is not particularly limited and may optionally be selected from a wide range, but it is usually from 1 to 70 wt %, preferably from 5 to 50 wt % in the entire composition.

The administration method of the preventive or therapeutic medicines for diabetes of the present invention is not particularly limited, and they are orally or parenterally administered by a method depending upon the form of the preparation, the age, the sex or other conditions of the patient and the degree of the disease. For example, for oral administration, a tablet, a pill, a solution, a suspension, an emulsion, a granule or a capsule may, for example, be mentioned as a preferred form. For parenteral administration, the medicine may be administered in the form of e.g. a topical agent, an injection, a transdermal agent, a transnasal formulation, a pulmonary delivery formulation or a suppository. In the case of an injection, it is preferred that the medicine is intravenously administered by itself or as mixed with a conventional fluid replacement such as glucose or amino acids, or as the case requires, it is intramuscularly, intradermally, subcutaneously or intraperitoneally administered by itself. Further, in the case of a suppository, it is preferred that the medicine is administered in rectum. The dose of the preventive or therapeutic medicines for diabetes of the present invention is optionally selected depending upon e.g. the dose regimen, the age, the sex or other conditions of the patient and the degree of disease, and usually the amount of the compound of the above formula (I) as an active ingredient is preferably from about 0.05 to about 50 mg per kg of the body weight per day, and the medicine may be administered once or several times a day. Further, it is preferred that the active ingredient is contained in an amount of from 1 to 1,000 mg in the administration unit form.

The compounds of the above formula (I) and their salts can be produced by a process for producing known analogous compounds, or a method in accordance therewith, and as preferred embodiments, the following Preparation Methods [1] to [5] will be exemplified.

[1] Preparation Method 1

A method for producing the compound of the above formula (I) by reacting a compound of the formula (II):

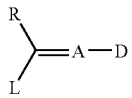

[wherein R is $R^1$ or $R^2$ in the formula (I), A is as defined above, D is a cyano group or an alkoxycarbonyl group, and L is a leaving group], with a compound of the formula (III):

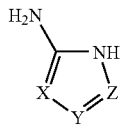

[wherein X, Y and Z are as defined above]. As the leaving group represented by L in the formula (II), various ones may be mentioned, and a halogen atom, a —$OR^5$ group, a —$SR^5$ group or a dialkylamino group is preferred ($R^5$ is as defined above).

The reaction of the Preparation Method 1 may be carried out in the presence of a proper solvent. The specific solvent used may, for example, be an alcohol such as methanol, ethanol, propanol or butanol; an aromatic hydrocarbon such as benzene, toluene or xylene; an aliphatic hydrocarbon such as pentane, hexane, heptane, petroleum ether, ligroin or petroleum benzine; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethylsulfoxide; a sulfone such as sulfolane; a phosphate amide such as hexamethylphosphoramide; or a halogenated hydrocarbon such as chloroform, dichloromethane, carbon tetrachloride or 1,2-dichloroethane, or a mixed solvent thereof.

In the Preparation Method 1, the reaction is carried out preferably in the presence of a base in some cases. The specific base used may, for example, be an organic base such as triethylamine, pyridine, piperidine, N-methylmorpholine, 1,8-diazabicyclo[5,4,0]-7-undecene or N,N-dimethylaniline; an alkali metal such as lithium, sodium or potassium; a carbonate of an alkali metal such as lithium carbonate, sodium carbonate or potassium carbonate; a hydrogencarbonate of an alkali metal such as lithium hydrogencarbonate, sodium hydrogencarbonate or potassium hydrogencarbonate; a hydride of an alkali metal such as lithium hydride, sodium hydride or potassium hydride; or n-butyllithium, lithium diisopropylamide or sodium amide.

The reaction of the Preparation Method 1 is carried out usually at a reaction temperature of from 0 to 150° C., preferably at a reaction temperature of from 10 to 100° C. The reaction time is usually from 0.1 to 48 hours.

In the Preparation Method 1, the compound of the formula (III) may be used in an amount of from 0.8 to 2 equivalents, preferably from 1 to 1.5 equivalents, per 1 mol of the compound of the above formula (II).

In the Preparation Method 1, various reaction conditions may optionally be combined with one another. Further, such various reaction conditions include reaction conditions in a usual range and reaction conditions in a preferred range, and they may also be optionally selected and combined with one another.

[2] Preparation Method 2

A method for producing the compound of the above formula (I) by reacting a compound of the formula (I-1):

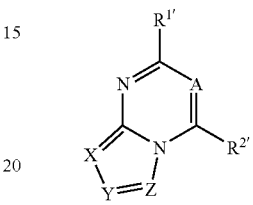

[wherein either one of $R^{1'}$ and $R^{2'}$ is an amino group, OH or SH; and the other is a hydrogen atom, a halogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, a —$B^1$—$R^5$ group (wherein $B^1$ and $R^5$ are as defined above), an amino group which may be substituted or —$N$=$CR^6R^7$ (wherein $R^6$ and $R^7$ are as defined above); and A, X, Y and Z are as defined above], with a compound of the formula (IV): R'—L' [wherein R' is an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted or a —$B^{1''}$—$R^{5'}$ group (wherein $B^{1''}$ is CO or $SO_2$, and $R^{5'}$ is an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted); and L' is a leaving group]. As the leaving group represented by L' in the formula (IV), various ones may be mentioned, and a halogen atom, a methanesulfonyloxy group or a para-toluenesulfonyloxy group is preferred.

The reaction of the Preparation Method 2 may be carried out in the presence of a proper solvent. The specific solvent used may, for example, be an aromatic hydrocarbon such as benzene, toluene or xylene; an aliphatic hydrocarbon such as pentane, hexane, heptane, petroleum ether, ligroin or petroleum benzine; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethylsulfoxide; a sulfone such as sulfolane; a phosphate amide such as hexamethylphosphoramide; or a halogenated hydrocarbon such as chloroform, dichloromethane, carbon tetrachloride or 1,2-dichloroethane, or a mixed solvent thereof.

In the Preparation Method 2, the reaction is carried out preferably in the presence of a base, so as to carry out the reaction efficiently. The specific base used may, for example, be an organic base such as triethylamine, pyridine, N-methylmorpholine, 1,8-diazabicyclo[5,4,0]-7-undecene or N,N-dimethylaniline; an alkali metal such as lithium, sodium or potassium; a carbonate of an alkali metal such as lithium carbonate, sodium carbonate or potassium carbonate; a hydrogencarbonate of an alkali metal such as lithium hydrogencarbonate, sodium hydrogencarbonate or potassium hydrogencarbonate; a hydride of an alkali metal such as lithium hydride, sodium hydride or potassium hydride; or n-butyllithium, lithium diisopropylamide or sodium amide.

The reaction of the Preparation Method 2 is carried out usually at a reaction temperature of from −70 to 200° C., preferably at a reaction temperature of from −10 to 150° C. The reaction time is usually from 0.1 to 48 hours.

In the Preparation Method 2, the compound of the formula (IV) may be used in an amount of from 0.8 to 2 equivalents, preferably from 1 to 1.5 equivalents, per 1 mol of the compound of the above formula (I-1).

In the Preparation Method 2, various reaction conditions may optionally be combined with one another. Further, such various reaction conditions include reaction conditions in a usual range and reaction conditions in a preferred range, and they may also be optionally selected and combined with one another.

[3] Preparation Method 3

A method for producing the compound of the above formula (I) by reacting a compound of the formula (I-2):

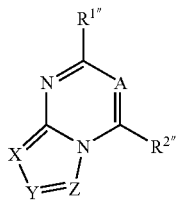

[wherein either one of $R^{1''}$ and $R^{2''}$ is OH, and the other is a hydrogen atom, a halogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, a —$B^1$—$R^5$ group (wherein $B^1$ and $R^5$ are as defined above), an amino group which may be substituted or —N=$CR^6R^7$ (wherein $R^6$ and $R^7$ are as defined above); and A, X, Y and Z are as defined above], with a halogenating agent.

The halogenating agent used in the reaction of the Preparation Method 3 may, for example, be phosphorus pentachloride, phosphorus oxychloride, phosphorus trichloride, thionyl chloride, oxalyl chloride or phenylphosphonate dichloride, and its amount is from 1 to 10 equivalents, preferably from 1 to 5 equivalents, per 1 mol of the compound of the above formula (I-2).

The reaction of the Preparation Method 3 may be carried out in the presence of a proper solvent. The specific solvent used may, for example, be an aromatic hydrocarbon such as benzene, toluene or xylene; an aliphatic hydrocarbon such as pentane, hexane, heptane, petroleum ether, ligroin or petroleum benzine; an ether such as diethyl ether, dipropyl ether, dibutyl ether, tetrahydrofuran or dioxane; or a halogenated hydrocarbon such as chloroform, dichloromethane, carbon tetrachloride or 1,2-dichloroethane, or a mixed solvent thereof. The reaction is carried out preferably in the system in which no water is present.

In the Preparation Method 3, the reaction is carried out preferably in the presence of a base, so as to carry out the reaction efficiently. The specific base used may, for example, be an organic base such as triethylamine, pyridine, N-methylmorpholine, 1,8-diazabicyclo[5,4,0]-7-undecene or N,N-dimethylaniline.

The reaction of the Preparation Method 2 is carried out usually at a reaction temperature of from −30 to 200° C., preferably at a reaction temperature of from 0 to 150° C. The reaction time is usually from 0.1 to 48 hours.

In the Preparation Method 3, various reaction conditions may optionally be combined with one another. Such various reaction conditions include reaction conditions in a usual range and reaction conditions in a preferred range, and they may also be optionally selected and combined with one another.

[4] Preparation Method 4

A method for producing the compound of the above formula (I) by reacting a compound of the formula (I-3):

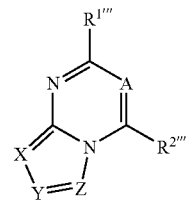

[wherein either one of $R^{1'''}$ and $R^{2'''}$ is a halogen atom, a —$B^{1'''}$—$R^{5'}$ group (wherein $B^{1'''}$ is O, $OSO_2$, S or $SO_2$, and $R^{5'}$ is an alkyl group which may be substituted or an aryl group which may be substituted) or a dialkylamino group, and the other is a hydrogen atom, a halogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, a —$B^1$—$R^5$ group (wherein $B^1$ and $R^5$ are as defined above), an amino group which may be substituted or —N=$CR^6R^7$ (wherein $R^6$ and $R^7$ are as defined above); and A, X, Y and Z are as defined above], with a compound of the formula (V): R''—B''' [wherein R'' is an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted, and B''' is an amino group, OH or SH].

The reaction of the Preparation Method 4 may be carried out in the presence of a proper solvent. The specific solvent used may, for example, be an aromatic hydrocarbon such as benzene, toluene or xylene; an aliphatic hydrocarbon such as pentane, hexane, heptane, petroleum ether, ligroin or petroleum benzine; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethylsulfoxide; a sulfone such as sulfolane; a phosphate amide such as hexamethylphosphoramide; or a halogenated hydrocarbon such as chloroform, dichloromethane, carbon tetrachloride or 1,2-dichloroethane, or a mixed solvent thereof.

In the Preparation Method 4, the reaction is carried out preferably in the presence of a base, so as to carry out the reaction efficiently. The specific base used may, for example, be an organic base such as triethylamine, pyridine, N-methylmorpholine, 1,8-diazabicyclo[5,4,0]-7-undecene or N,N-dimethylaniline; an alkali metal such as lithium, sodium or potassium; a carbonate of an alkali metal such as lithium carbonate, sodium carbonate or potassium carbonate; a hydrogencarbonate of an alkali metal such as lithium hydrogencarbonate, sodium hydrogencarbonate or potassium hydrogencarbonate; a hydride of an alkali metal such as lithium hydride, sodium hydride or potassium hydride; or n-butyllithium, lithium diisopropylamide or sodium amide.

The reaction of the Preparation Method 4 is carried out usually at a reaction temperature of from −70 to 150° C., preferably at a reaction temperature of from −10 to 100° C. The reaction time is usually from 0.1 to 48 hours.

In the Preparation Method 4, the compound of the formula (V) may be used in an amount of from 0.8 to 2 equivalents, preferably from 1 to 1.5 equivalents, per 1 mol of the compound of the above formula (I-3).

In the Preparation Method 3, various reaction conditions may optionally be combined with one another. Further, such various reaction conditions include reaction conditions in a usual range and reaction conditions in a preferred range, and they may also be optionally selected and combined with one another.

[5] Preparation Method 5

A method for producing the compound of the above formula (I) by reacting a compound of the formula (I-4):

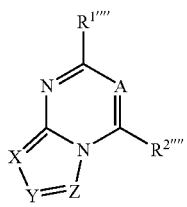

[wherein either one of $R^{1''''}$ and $R^{2''''}$ is an amino group, and the other is a hydrogen atom, a halogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted, a heterocyclic group which may be substituted, a —$B^1$—$R^5$ group (wherein $B^1$ and $R^5$ are as defined above), an amino group which may be substituted or —N=$CR^6R^7$ (wherein $R^6$ and $R^7$ are as defined above); and A, X, Y and Z are as defined above], with a compound of the formula (VI): $R^6R^7C$=O [wherein $R^6$ and $R^7$ are as defined above].

The reaction of the Preparation Method 5 may be carried out in the presence of a proper solvent. The specific solvent used may, for example, be an alcohol such as methanol, ethanol, propanol or butanol; an aromatic hydrocarbon such as benzene, toluene or xylene; an aliphatic hydrocarbon such as pentane, hexane, heptane, petroleum ether, ligroin or petroleum benzine; an ether such as diethyl ether, dipropyl ether, dibutyl ether, tetrahydrofuran or dioxane; a nitrile such as acetonitrile or propionitrile; an acid amide such as dimethylformamide or dimethylacetamide; a sulfoxide such as dimethylsulfoxide; a sulfone such as sulfolane; a phosphate amide such as hexamethylphosphoramide; or a halogenated hydrocarbon such as chloroform, dichloromethane, carbon tetrachloride or 1,2-dichloroethane, or a mixed solvent thereof.

In the Preparation Method 5, the reaction is carried out preferably in the presence of a base, so as to carry out the reaction efficiently. The specific base used may, for example, be an organic base such as triethylamine, pyridine, N-methylmorpholine, 1,8-diazabicyclo[5,4,0]-7-undecene or N,N-dimethylaniline; a carbonate of an alkali metal such as lithium carbonate, sodium carbonate or potassium carbonate; or a hydrogencarbonate of an alkali metal such as lithium hydrogencarbonate, sodium hydrogencarbonate or potassium hydrogencarbonate.

In the Preparation Method 5, the reaction is carried out preferably in the presence of a dehydrating agent such as molecular sieves, so as to carry out the reaction efficiently. Further, a proper solvent may be used to remove formed moisture from the reaction system by azeotropy.

The reaction of the Preparation Method 5 is carried out usually at a reaction temperature of from −30 to 150° C., preferably at a reaction temperature of from 0 to 100° C. The reaction time is usually from 0.1 to 48 hours.

In the Preparation Method 5, the compound of the formula (VI) may be used in an amount of from 0.8 to 2 equivalents, preferably from 1 to 1.5 equivalents, per 1 mol of the compound of the above formula (I-3).

In the Preparation Method 5, various reaction conditions may optionally be combined with one another. Further, such various reaction conditions include reaction conditions in a usual range and reaction conditions in a preferred range, and they may also be optionally selected and combined with one another.

The compounds of the above formula (I) and their salts may be produced by any one of the above Preparation Methods [1] to [5] or a combination thereof.

The compounds of the above formula (I) may form salts by a conventional method. Further, the compounds of the above formula (I) may form inner salts in some cases.

Among the compounds of the above formula (I) and their salts, compounds having a carboxyl group in their molecular structures and their salts may be produced by hydrolyzing corresponding esters under an acid or alkali condition.

Among the compounds of the above formula (I) and their salts, compounds of the formula (I') and their salts may be produced by one of the following Preparation Methods [A] to [G] or a combination of these Preparation Methods, in accordance with the above Preparation Methods 1 to 5.

[A]

Among the compounds of the above formula (I') and their salts, compounds of the formula (I'-1) and their salts:

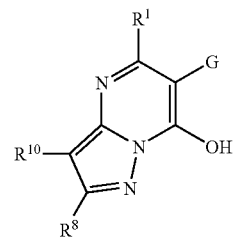

[wherein $R^1$, $R^8$, $R^{10}$ and G are as defined in the above formula (I')], can be produced by reacting a compound of the formula (VII):

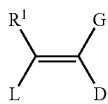

[wherein $R^1$ and G are as defined above; D is an alkoxycarbonyl group; and L is a halogen atom, a —$OR^5$ group, a —$SR^5$ group or a dialkylamino group ($R^5$ is as defined above)], with a compound of the formula (VIII):

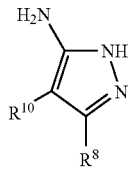

[wherein $R^8$ and $R^{10}$ are as defined above]. The Preparation Method [A] is in accordance with the Preparation Method 1, and various reaction conditions in the Preparation Method 1 can be applied.

[B]

Among the compounds of the above formula (I') and their salts, compounds of the formula (I'-2) and their salts:

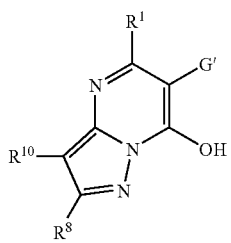

[wherein $R^1$, $R^8$ and $R^{10}$ are as defined in the above formula (I'); and G' is CN, $NO_2$, $SO_2NR^aR^b$ (wherein $R^a$ and $R^b$ are as defined above) or $CONR^aR^b$ (wherein $R^a$ and $R^b$ are as defined above)], can be produced by reacting a compound of the formula (VII'):

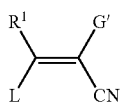

[wherein $R^1$ and G' are as defined above; and L is a halogen atom, a —$OR^5$ group, a —$SR^5$ group or a dialkylamino group ($R^5$ is as defined above)], with a compound of the formula (VIII):

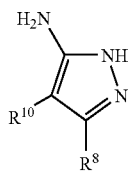

[wherein $R^8$ and $R^{10}$ are as defined above]. The Preparation Method [B] is in accordance with the Preparation Method 1, and various reaction conditions in the Preparation Method 1 can be applied.

[C]

Among the compounds of the above formula (I') and their salts, compounds of the formula (I'-3) and their salts:

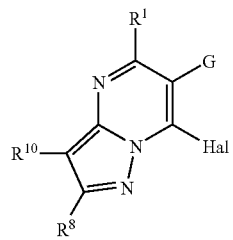

[wherein $R^1$, $R^8$, $R^{10}$ and G are as defined in the above formula (I')], can be produced by reacting the compound of the formula (I'-1) produced by the method as defined in the Preparation Method [A] with a halogenating agent. The Preparation Method [C] is in accordance with the Preparation Method 3, and various reaction conditions in the Preparation Method 3 can be applied.

[D]

Among the compounds of the above formula (I') and their salts, compounds of the formula (I'-4) and their salts:

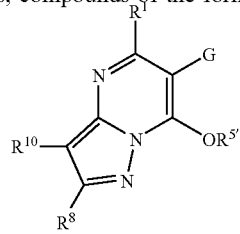

[wherein $R^1$, $R^8$, $R^{10}$ and G are as defined in the above formula (I'); and $R^5$ is an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted], can be produced by reacting the compound of the formula (I'-1) produced by the method as defined in the Preparation Method [A] with a compound of the formula (IX): $R^{5'}$-L' [wherein $R^{5'}$ is as defined above; and L' is a halogen atom, a methanesulfonyloxy group or a para-toluenesulfonyloxy group]. The Preparation Method [D] is in accordance with the Preparation Method 2, and various reaction conditions in the Preparation Method 2 can be applied.

[E]

Among the compounds of the above formula (I') and their salts, compounds of the formula (I'-5) and their salts:

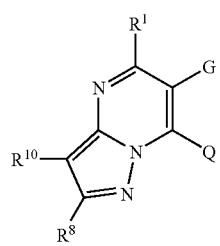

[wherein $R^1$, $R^8$, $R^{10}$ and G are as defined in the above formula (I'); and Q is a substituted amino group], can be produced also by reacting the compound of the formula (I'-3) produced by the method as defined in the Preparation Method [C] with a compound of the formula (IV-1): H-Q [wherein Q is a substituted amino group]. The Preparation Method [E] is in accordance with the Preparation Method 4, and various reaction conditions in the Preparation Method 4 can be applied.

[F]

Further, the compounds of the formula (I'-5) and their salts can be produced also by reacting the compound of the formula (I'-4) produced by the method as defined in the Preparation Method [D] with the compound of the formula (IV-1). The Preparation Method [F] is in accordance with the Preparation Method 4, and various reaction conditions in the Preparation Method 4 can be applied.

[G]

Further, among the compounds of the above formula (I'-5) and their salts, compounds of the formula (I'-5') and their salts:

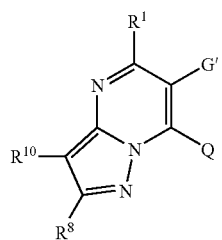

[wherein $R^1$, $R^8$, $R^{10}$ and Q are as defined in the above formula (I'-5); and G' is as defined in the above formula (I'-2)], can be produced by reacting the compound of the formula (I'-2) produced by the method as defined in the Preparation Method [B] with a compound of the formula (IV-2): L'-J [wherein J is a substituent of the substituted amino group represented by Q; and L' is a halogen atom, a methanesulfonyloxy group or a para-toluenesulfonyloxy group]. The Preparation Method [G] is in accordance with the Preparation Method 2, and various reaction conditions in the Preparation Method 2 can be applied.

EXAMPLES

Now, Examples (Preparation Examples and Test Examples) of the present invention will be described, however, the present invention is by no means restricted thereto.

Preparation Example 1

Preparation of 7-benzylamino-5-methylthiopyrazolo [1,5-a]pyrimidine-6-carbonitrile (Compound No. 2)

(1) 10.3 g of bismethylthio methylenepropane dinitrile, 5.0 g of 3-aminopyrazole and 250 ml of ethanol were stirred under reflux with heating for about 6 hours and then cooled to room temperature, and the precipitated crystals were collected by filtration. The collected crystals were washed with ethanol and then dried to obtain 10.9 g of 7-amino-5-methylthiopyrazolo[1,5-a]pyrimidine-6-carbonitrile (compound No. 1) having a melting point of at least 240° C.

(2) 100 mg of sodium hydride (60%) was added to 500 mg of 7-amino-5-methylthiopyrazolo[1,5-a]pyrimidine-6-carbonitrile and 8 ml of DMF, followed by stirring at room temperature for about 10 minutes, and then 420 mg of benzyl bromide was added thereto, followed by stirring at about 50° C. for about 2 hours. After completion of the reaction, the reaction mixture was cooled to room temperature, about 50 ml of water was added thereto, and the precipitated crystals were collected by filtration, washed with water and dried to obtain crude crystals. The crude crystals were purified by silica gel column chromatography to obtain 570 mg of 7-benzylamino-5-methylthiopyrazolo [1,5-a]pyrimidine-6-carbonitrile (compound No. 2) having a melting point of 165° C.

Preparation Example 2

Preparation of 7-benzyloxy-5-methylthiopyrazolo[1, 5-a]pyrimidine-6-carbonitrile (Compound No. 51)

(1) 3.0 g of 2-cyano-3,3-bismethylthio-2-propenoic acid methyl ester, 1.3 g of 3-aminopyrazole and 20 ml of ethanol were stirred under reflux with heating for about 2.5 hours and then cooled to room temperature, and the precipitated crystals were collected by filtration. The collected crystals were washed with ethanol and then dried to obtain 1.69 g of 7-hydroxy-5-methylthiopyrazolo[1,5-a]pyrimidine-6-carbonitrile (compound No. 49) having a melting point of over 250° C.

(2) 80 mg of sodium hydride (60%) was added to 400 mg of 7-hydroxy-5-methylthiopyrazolo[1,5-a]pyrimidine-6-carbonitrile and 6 ml of DMF, followed by stirring at room temperature for about 10 minutes, and then 350 mg of benzyl bromide was added thereto, followed by stirring at about 50° C. overnight. After completion of the reaction, the reaction mixture was cooled to room temperature, about 50 ml of water was added thereto, and the precipitated crystals were collected by filtration, washed with water and dried to obtain crude crystals. The crude crystals were purified by silica gel column chromatography to obtain 490 mg of 7-benzyloxy-5-methylthiopyrazolo[1,5-a]pyrimidine-6-carbonitrile (compound No. 51) having a melting point of 194° C.

Preparation Example 3

Preparation of 7-(4-pyridylmethyl)amino-5-methylthiopyrazolo[1,5-a]pyrimidine-6-carbonitrile (Compound No. 3)

(1) A mixture comprising 2.15 g of 7-hydroxy-5-methylthiopyrazolo[1,5-a]pyrimidine-6-carbonitrile (compound No. 49), 1.3 g of N,N-dimethylaniline and 5 ml of phosphorus oxychloride was stirred under reflux with heating for about 3 hours. After the completion of the reaction, the reaction mixture was cooled to room temperature, and poured into ice water, followed by stirring. The precipitated crystals were collected by filtration, washed with water and dried to obtain crude crystals. The crude crystals were purified by silica gel column chromatography to obtain 2.17 g of 7-chloro-5-methylthiopyrazolo[1,5-a]pyrimidine-6-carbonitrile (compound No. 62) having a melting point of from 201 to 202° C.

(2) A mixture comprising 460 mg of 4-picolylamine, 430 mg of triethylamine and 1 ml of acetonitrile was dropwise added to 950 mg of 7-chloro-5-methylthiopyrazolo[1,5-a] pyrimidine-6-carbonitrile and 20 ml of acetonitrile under cooling with ice, followed by stirring for about 1 hour. After completion of the reaction, about 80 ml of water was added thereto, and the precipitated crystals were collected by filtration, washed with water and dried to obtain crude crystals. The crude crystals were purified by silica gel column chromatography to obtain 970 mg of 7-(4-pyridylmethyl)amino-5-methylthiopyrazolo[1,5-a]pyrimidine-6-carbonitrile (compound No. 3) having a melting point of from 153 to 154° C.

Preparation Example 4

Preparation of 7-furfurylamino-5-methylthiopyrazolo[1,5-a]pyrimidine-6-carbonitrile (Compound No. 78)

200 mg of 7-chloro-5-methylthiopyrazolo[1,5-a]pyrimidine-6-carbonitrile (compound No. 62) and 100 mg of furfurylamine were reacted in 5 ml of THF in the presence of 110 mg of triethylamine for about 30 minutes, then about 30 ml of water was added thereto, and the precipitated crystals were collected by filtration, washed with water and dried to obtain crude crystals. The crude crystals were washed with ether to obtain 180 mg of 7-furfurylamino-5-methylthiopyrazolo[1,5-a]pyrimidine-6-carbonitrile (compound No. 78) having a melting point of 110° C.

Compounds of the above formula (I) produced in Preparation Examples 1 to 4 and by methods in accordance with the above Preparation Methods 1 to 5 are shown in the following Tables 1 to 26.

TABLE 1

| Compound No. | Structural Formula | Physical properties |
| --- | --- | --- |
| 1 | SMe, CN, NH₂ | m.p. >240° C. |
| 2 | SMe, CN, NHCH₂Ph | m.p.: 165° C. |
| 3 | SMe, CN, NH-CH₂-(4-pyridyl) | m.p.: 153–154° C. |
| 4 | SMe, CN, NH-CH₂-(3-pyridyl) | m.p.: 192° C. |
| 5 | SMe, CN, NH-CH₂-(2-pyridyl) | m.p.: 190° C. |
| 6 | SMe, CN, N(CH₂-(2-pyridyl))₂ | m.p.: 139° C. |
| 7 | SMe, CN, NHCOMe | m.p. >280° C. |
| 8 | SMe, CN, NH-CH₂-(1,3-dioxolan-2-yl) | m.p.: 157–158° C. |
| 9 | SMe, CN, NHCH₂OEt | m.p.: 132–133° C. |

TABLE 2

| Compound No. | Structural Formula | Physical properties |
|---|---|---|
| 10 | SMe, CN, NHCH₂OCH₂Ph substituents on pyrazolo[1,5-a]pyrimidine | m.p.: 63–64° C. |
| 11 | SMe, CN, NH-CH₂-(tetrahydropyran-2-yl) substituents on pyrazolo[1,5-a]pyrimidine | m.p.: 121–122° C. |
| 12 | SMe, CN, NHCH₂CH₂Ph substituents on pyrazolo[1,5-a]pyrimidine | m.p.: 107° C. |
| 13 | SMe, CN, NHCH₂COOEt substituents on pyrazolo[1,5-a]pyrimidine | m.p.: 184–185° C. |
| 14 | SMe, CN, NHMe substituents on pyrazolo[1,5-a]pyrimidine | m.p.: 216° C. |
| 15 | SMe, CN, NHEt substituents on pyrazolo[1,5-a]pyrimidine | m.p.: 133° C. |
| 16 | SMe, CN, NH-CH₂-(4-NO₂-C₆H₄) substituents on pyrazolo[1,5-a]pyrimidine | m.p.: 215° C. |

TABLE 2-continued

| Compound No. | Structural Formula | Physical properties |
|---|---|---|
| 17 | SMe, CN, NMe₂ substituents on pyrazolo[1,5-a]pyrimidine | m.p.: 144° C. |
| 18 | SMe, CN, NHCH₂COPh substituents on pyrazolo[1,5-a]pyrimidine | m.p.: 212–213° C. |

TABLE 3

| Compound No. | Structural Formula | Physical properties |
|---|---|---|
| 19 | SMe, CN, NHCH₂CH₂CHMe₂ substituents on pyrazolo[1,5-a]pyrimidine | m.p.: 87–88° C. |
| 20 | SMe, CN, NHCH₂COBu(t) substituents on pyrazolo[1,5-a]pyrimidine | m.p.: 164–165° C. |
| 21 | SMe, CN, N(CH₂C≡CH)₂ substituents on pyrazolo[1,5-a]pyrimidine | m.p.: 141° C. |
| 22 | Me, CN, NHCH₂C≡CH substituents on pyrazolo[1,5-a]pyrimidine | m.p.: 169° C. |

TABLE 3-continued

| Compound No. | Physical Structural Formula | Physical properties |
|---|---|---|
| 23 | 5-SMe, 6-CN, 7-NHCH2-C6H4-4-COOMe pyrazolo[1,5-a]pyrimidine | m.p.: 171° C. |
| 24 | 6-CN, 7-NH2 pyrazolo[1,5-a]pyrimidine | m.p.: >250° C. |
| 25 | 5-Me, 6-CN, 7-NH2 pyrazolo[1,5-a]pyrimidine | m.p.: >250° C. |
| 26 | 5-Me, 6-CN, 7-NHCH2CH2OMe2 pyrazolo[1,5-a]pyrimidine | m.p.: 135° C. |
| 27 | 5-Me, 6-CN, 7-NHCH2CH2Ph pyrazolo[1,5-a]pyrimidine | m.p.: 143° C. |

TABLE 4

| Compound No. | Structural Formula | Physical properties |
|---|---|---|
| 28 | 6-CN, 7-NHCH2Ph pyrazolo[1,5-a]pyrimidine | m.p.: 125° C. |
| 29 | 5-Me, 6-CN, 7-NHCH2-(4-pyridyl) pyrazolo[1,5-a]pyrimidine | m.p.: 165° C. |

TABLE 4-continued

| Compound No. | Structural Formula | Physical properties |
|---|---|---|
| 30 | 5-SMe, 6-CN, 7-NHCH2-(1-naphthyl) pyrazolo[1,5-a]pyrimidine | m.p.: 195° C. |
| 31 | 5-SMe, 6-CN, 7-NHCH2-C6H4-4-Cl pyrazolo[1,5-a]pyrimidine | m.p.: 167° C. |
| 32 | 5-SMe, 6-CN, 7-NHCH2-C6H4-3-Cl pyrazolo[1,5-a]pyrimidine | m.p.: 155° C. |
| 33 | 5-SMe, 6-CN, 7-NHCH2-C6H4-2-Cl pyrazolo[1,5-a]pyrimidine | m.p.: 160° C. |
| 34 | 5-SMe, 6-CN, 7-N=CHPh pyrazolo[1,5-a]pyrimidine | m.p.: 188° C. |
| 35 | 5-SMe, 6-CN, 7-NH2, 2-MeS [1,2,4]triazolo[1,5-a]pyrimidine | m.p.: >250° C. |

TABLE 4-continued

| Compound No. | Structural Formula | Physical properties |
|---|---|---|
| 36 | (structure: SMe, CN, NHCH2Ph, MeS substituents on fused triazolo-pyrimidine) | m.p.: 154° C. |

TABLE 5

| Compound No. | Structural Formula | Physical properties |
|---|---|---|
| 37 | (SMe, NH2 on pyrazolo-triazine) | m.p.: 211° C. |
| 38 | (SMe, CN, NHCH2-4-pyridyl, MeS on pyrazolo-triazolo-pyrimidine) | m.p.: 230–233° C. |
| 39 | (SMe, NHCH2Ph on pyrazolo-triazine) | m.p.: 133° C. |
| 40 | (SMe, NH-CH2-4-pyridyl on pyrazolo-triazine) | m.p.: 136° C. |
| 41 | (SMe, CN, NH2 on pyrazolo-pyrimidine) | m.p.: >250° C. |
| 42 | (SMe, CN, NHCH2Ph on imidazo-pyrimidine) | m.p.: 179° C. |
| 43 | (SMe, CN, NH-CH2-4-pyridyl on imidazo-pyrimidine) | m.p.: 204° C. |
| 44 | (SMe, CN, NH2, Ph on pyrazolo-pyrimidine) | m.p.: 233° C. |
| 45 | (SMe, CN, NH2 on pyrimido-benzimidazole) | m.p.: >250° C. |

TABLE 6

| Compound No. | Structural Formula | Physical properties |
|---|---|---|
| 46 | (SMe, CN, NHCH2Ph, Ph on pyrazolo-pyrimidine) | m.p.: 172° C. |

TABLE 6-continued

| Compound No. | Structural Formula | Physical properties |
|---|---|---|
| 47 | SMe, CN, NHCH2Ph (pyrimido-benzimidazole) | m.p.: 233° C. |
| 48 | SMe, CN, NH-CH2-(4-pyridyl), Ph on pyrazolopyrimidine | m.p.: 232° C. |
| 49 | SMe, CN, OH on pyrazolopyrimidine | m.p. >250° C. |
| 50 | SMe, CN, NH-CH2-(4-methylphenyl) on pyrazolopyrimidine | m.p.: 159° C. |
| 51 | SMe, CN, OCH2Ph on pyrazolopyrimidine | m.p.: 194° C. |
| 52 | SMe, SO2Ph, NH2 on pyrazolopyrimidine | Solid |
| 53 | SMe, CN, OCH2C≡CH on pyrazolopyrimidine | m.p.: 183° C. |

TABLE 6-continued

| Compound No. | Structural Formula | Physical properties |
|---|---|---|
| 54 | SMe, CN, Br, NH2 on pyrazolopyrimidine | m.p. >250° C. |

TABLE 7

| Compound No. | Structural Formula | Physical properties |
|---|---|---|
| 55 | SMe, CN, Br, NHCH2Ph on pyrazolopyrimidine | m.p.: 184° C. |
| 56 | SMe, CN, NH-CH2-(4-methoxyphenyl) on pyrazolopyrimidine | m.p.: 137° C. |
| 57 | SMe, CN, NHCH2C≡CMe on pyrazolopyrimidine | m.p.: 155–157° C. |
| 58 | SMe, SO2Me, NH2 on pyrazolopyrimidine | m.p.: 230–233° C. |
| 59 | SMe, SO2Me, NHCH2C≡CH on pyrazolopyrimidine | m.p.: 175° C. |

TABLE 7-continued

| Compound No. | Structural Formula | Physical properties |
|---|---|---|
| 60 | SMe, SO₂Ph, NHCH₂C≡CH pyrazolopyrimidine | m.p.: 162–163° C. |
| 61 | SMe, SO₂Me, NHCH₂Ph pyrazolopyrimidine | m.p.: 163–164° C. |
| 62 | SMe, CN, Cl pyrazolopyrimidine | m.p.: 201–202° C. |
| 63 | SMe, SO₂Me, NH-CH₂-(4-pyridyl) pyrazolopyrimidine | m.p.: 195–196° C. |

TABLE 8

| Compound No. | Structural Formula | Physical properties |
|---|---|---|
| 64 | SMe, NHCH₂C≡CH pyrazolotriazine | m.p.: 175° C. |
| 65 | SMe, N(CH₂C≡CH)₂ pyrazolotriazine | m.p.: 113° C. |
| 66 | SEt, CN, NH₂ pyrazolopyrimidine | m.p. >240° C. |
| 67 | SEt, CN, NHCH₂Ph pyrazolopyrimidine | m.p.: 112–113.4° C. |
| 68 | SEt, CN, NH-CH₂-(4-pyridyl) pyrazolopyrimidine | m.p.: 196–196.4° C. |
| 69 | SCH₂Ph, CN, NH₂ pyrazolopyrimidine | m.p.: 245.6–245.9° C. |
| 70 | SCH₂Ph, CN, NHCH₂Ph pyrazolopyrimidine | m.p.: 121–122.2° C. |
| 71 | SCH₂Ph, CN, NH-CH₂-(4-pyridyl) pyrazolopyrimidine | m.p.: 187.8–189.2° C. (decomposition) |
| 72 | SPr(i), CN, NH₂ pyrazolopyrimidine | m.p. >240° C. |

TABLE 9
| Compound No. | Structural Formula | Physical properties |
|---|---|---|
| 73 | 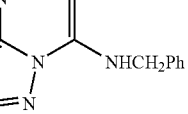 | m.p.: 114.7–115.2° C. |
| 74 | 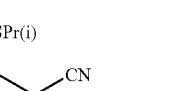 | m.p.: 134.5–135° C. |
| 75 | 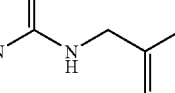 | m.p.: 258.5–259° C. |
| 76 | 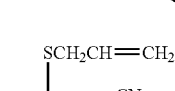 | m.p.: 178.8–179.8° C. |
| 77 | 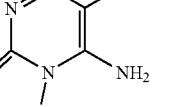 | m.p.: 90–91.5° C. |
| 78 | 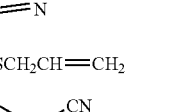 | m.p.: 110° C. |
| 79 | 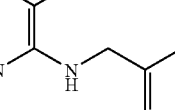 | m.p.: 118° C. |
TABLE 9-continued
| Compound No. | Structural Formula | Physical properties |
|---|---|---|
| 80 | 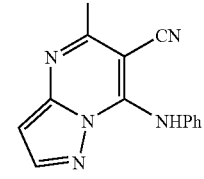 | m.p.: 195–196° C. |
| 81 | 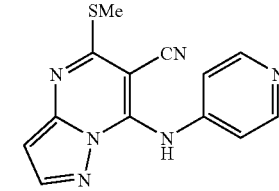 | m.p.: 260–263° C. |
TABLE 10
| Compound No. | Structural Formula | Physical properties |
|---|---|---|
| 82 | 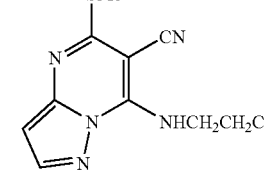 | m.p.: 188° C. |
| 83 | 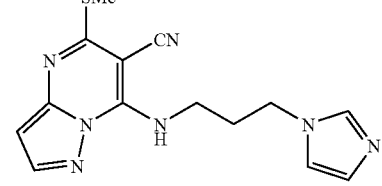 | m.p.: 144–146° C. |
| 84 | 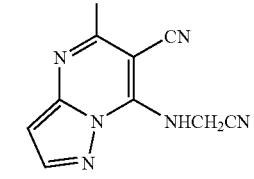 | m.p.: 207° C. |
| 85 | 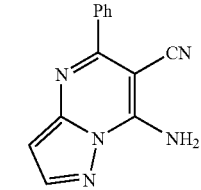 | m.p. >250° C. |

TABLE 10-continued

| Compound No. | Structural Formula | Physical properties |
|---|---|---|
| 86 | Ph, CN, NHCH2Ph pyrazolopyrimidine | m.p.: 120–122° C. |
| 87 | CH2Ph, CN, NH2 pyrazolopyrimidine | m.p.: 242° C. |
| 88 | CH2Ph, CN, NHCH2Ph pyrazolopyrimidine | m.p.: 163° C. |
| 89 | Ph, CN, NH-CH2-(4-pyridyl) pyrazolopyrimidine | m.p.: 199–201° C. |
| 90 | CH2Ph, CN, NH-CH2-(4-pyridyl) pyrazolopyrimidine | m.p.: 195–198° C. |

TABLE 11

| Compound No. | Structural Formula | Physical properties |
|---|---|---|
| 91 | cyclohexyl, CN, NH2 pyrazolopyrimidine | m.p. >250° C. |
| 92 | cyclohexyl, CN, NH-CH2-(2-pyridyl) pyrazolopyrimidine | |
| 93 | cyclohexyl, CN, NH-CH2-(4-pyridyl) pyrazolopyrimidine | |
| 94 | propargyl-S, CN, NH2 pyrazolopyrimidine | m.p.: 206° C. (decomposition) |
| 95 | propargyl-S, CN, NH-CH2Ph pyrazolopyrimidine | m.p.: 142.2–144.2° C. |
| 96 | propargyl-S, CN, NH-CH2-(4-pyridyl) pyrazolopyrimidine | m.p.: 208.5–208.7° C. |
| 97 | cyclopropyl-S, CN, NH2 pyrazolopyrimidine | |

TABLE 11-continued

| Compound No. | Structural Formula | Physical properties |
|---|---|---|
| 98 | (5-cyclopropylthio-7-benzylamino-pyrazolo[1,5-a]pyrimidine-6-carbonitrile) | |
| 99 | (5-cyclopropylthio-7-(pyridin-4-ylmethylamino)-pyrazolo[1,5-a]pyrimidine-6-carbonitrile) | |

TABLE 12

| Compound No. | Structural Formula | Physical properties |
|---|---|---|
| 100 | (5-SPh-7-amino-pyrazolo[1,5-a]pyrimidine-6-carbonitrile) | |
| 101 | (5-SPh-7-benzylamino-pyrazolo[1,5-a]pyrimidine-6-carbonitrile) | |
| 102 | (5-SPh-7-(pyridin-4-ylmethylamino)-pyrazolo[1,5-a]pyrimidine-6-carbonitrile) | |

TABLE 12-continued

| Compound No. | Structural Formula | Physical properties |
|---|---|---|
| 103 | (5-cyclopentylthio-7-amino-pyrazolo[1,5-a]pyrimidine-6-carbonitrile) | m.p.: 270.5–271.3° C. |
| 104 | (5-cyclopentylthio-7-benzylamino-pyrazolo[1,5-a]pyrimidine-6-carbonitrile) | m.p.: 115.8–116.6° C. |
| 105 | (5-cyclopentylthio-7-(pyridin-4-ylmethylamino)-pyrazolo[1,5-a]pyrimidine-6-carbonitrile) | m.p.: 153.4–155.4° C. |
| 106 | ($SCH_2OMe$ 7-amino-pyrazolo[1,5-a]pyrimidine-6-carbonitrile) | m.p.: 214–216° C. (decomposition) |
| 107 | ($SCH_2OMe$ 7-benzylamino-pyrazolo[1,5-a]pyrimidine-6-carbonitrile) | m.p.: 137.4–141.4° C. |
| 108 | ($SCH_2OMe$ 7-(pyridin-4-ylmethylamino)-pyrazolo[1,5-a]pyrimidine-6-carbonitrile) | m.p.: 164–165.5° C. (decomposition) |

TABLE 13

| Compound No. | Structural Formula | Physical properties |
|---|---|---|
| 109 | (pyrazolo[1,5-a]pyrimidine with SMe, CN, NH-cyclohexyl) | m.p.: 117–118° C. |
| 110 | (pyrazolo[1,5-a]pyrimidine with SBu(s), CN, NH₂) | m.p.: 241.7–242.1° C. |
| 111 | (pyrazolo[1,5-a]pyrimidine with SBu(s), CN, NH-benzyl) | m.p.: 94–96° C. |
| 112 | (pyrazolo[1,5-a]pyrimidine with SBu(s), CN, NH-CH₂-4-pyridyl) | m.p.: 113.5–118° C. |
| 113 | (pyrazolo[1,5-a]pyrimidine with SCHEt₂, CN, NH₂) | m.p.: 242.0–243.8° C. |
| 114 | (pyrazolo[1,5-a]pyrimidine with SCHEt₂, CN, NH-benzyl) | m.p.: 107.0–108.3° C. |
| 115 | (pyrazolo[1,5-a]pyrimidine with SCHEt₂, CN, NH-CH₂-4-pyridyl) | m.p.: 129.0–133.4° C. |

TABLE 13-continued

| Compound No. | Structural Formula | Physical properties |
|---|---|---|
| 116 | (pyrazolo[1,5-a]pyrimidine with SCH₃OEt, CN, NH₂) | m.p. >300° C. |
| 117 | (pyrazolo[1,5-a]pyrimidine with SCH₂OEt, CN, NHBn) | m.p.: 130.5–133.5° C. |

TABLE 14

| Compound No. | Structural Formula | Physical properties |
|---|---|---|
| 118 | (pyrazolo[1,5-a]pyrimidine with SCH₂OEt, CN, NH-CH₂-pyridyl) | m.p.: 160.0–161.6° C. |
| 119 | (pyrazolo[1,5-a]pyrimidine with SMe, COOMe, Cl) | m.p.: 105–113° C. |
| 120 | (pyrazolo[1,5-a]pyrimidine with SMe, COOMe, NHBn) | m.p.: 124.5–126.5° C. |
| 121 | (pyrazolo[1,5-a]pyrimidine with SMe, COOMe, NHBn) | m.p.: 158.5–160.5° C. |
| 122 | (pyrazolo[1,5-a]pyrimidine with SMe, COOMe, NHPh) | Oily matter |
| 123 | (pyrazolo[1,5-a]pyrimidine with SMe, COOMe, NH-cyclopentyl) | m.p.: 84.5–85.5° C. |
| 124 | (pyrazolo[1,5-a]pyrimidine with SMe, NO₂, Cl) | Solid |
| 125 | (pyrazolo[1,5-a]pyrimidine with SMe, NO₂, NHBn) | m.p.: 136.5–138.5° C. |

TABLE 14-continued

| Compound No. | Structural Formula | Physical properties |
|---|---|---|
| 126 | SMe, NO2, pyrazolo[1,5-a]pyrimidine with NH-CH2-(4-pyridyl) | m.p.: 154–155° C. |

TABLE 15

| Compound No. | Structural Formula | Physical properties |
|---|---|---|
| 127 | SMe, NO2, pyrazolo[1,5-a]pyrimidine with NH-cyclopentyl | m.p.: 132–134° C. |
| 128 | SMe, COOH, pyrazolo[1,5-a]pyrimidine with NH-CH2-phenyl | m.p.: 162.7–164° C. |
| 129 | SMe, COOH, pyrazolo[1,5-a]pyrimidine with NH-CH2-(4-pyridyl) | m.p.: 155–157° C. |
| 130 | SMe, COOHMe, pyrazolo[1,5-a]pyrimidine with NH-(4-CN-phenyl) | m.p.: 180.5–181.3° C. |
| 131 | SMe, COOHMe, pyrazolo[1,5-a]pyrimidine with NH-(3-CN-phenyl) | m.p.: 175.7–176.4° C. |

TABLE 15-continued

| Compound No. | Structural Formula | Physical properties |
|---|---|---|
| 132 | SMe, COOH, pyrazolo[1,5-a]pyrimidine with NH-O-CH2-phenyl | Oily matter |
| 133 | SMe, COOMe, pyrazolo[1,5-a]pyrimidine with NH-O-CH(1,3-dioxolane) | m.p.: 126.5–127.5° C. |
| 134 | SMe, COOH, pyrazolo[1,5-a]pyrimidine with NH-(3-CN-phenyl) | m.p.: 162.5–164.5° C. |
| 135 | OMe, CN, pyrazolo[1,5-a]pyrimidine with NH-CH2-phenyl | m.p.: 148.8–149.6° C. |

TABLE 16

| Compound No. | Structural Formula | Physical properties |
|---|---|---|
| 136 | OMe, CN, pyrazolo[1,5-a]pyrimidine with NH-CH2-(1,3-dioxolane) | m.p.: 148.3–149.7° C. |
| 137 | SMe, COOPr(n), pyrazolo[1,5-a]pyrimidine with Cl | m.p.: 55–56° C. |

TABLE 16-continued

| Compound No. | Structural Formula | Physical properties |
|---|---|---|
| 138 | SMe, COOPr(n), pyrazolo[1,5-a]pyrimidine with NH-CH2-(4-pyridyl) | m.p.: 100.5–101° C. |
| 139 | SMe, COOPr(n), pyrazolo[1,5-a]pyrimidine with NH-(3-cyanophenyl) | m.p.: 107–108.5° C. |
| 140 | SMe, COOPr(i), pyrazolo[1,5-a]pyrimidine with Cl | m.p.: 56–58° C. |
| 141 | SMe, COOPr(i), pyrazolo[1,5-a]pyrimidine with NH-CH2-(4-pyridyl) | m.p.: 111–112° C. |
| 142 | SMe, COOPr(i), pyrazolo[1,5-a]pyrimidine with NH-(3-cyanophenyl) | m.p.: 120–122° C. |
| 143 | SMe, COOBu(n), pyrazolo[1,5-a]pyrimidine with Cl | m.p.: 55–57° C. |
| 144 | SMe, COOBu(n), pyrazolo[1,5-a]pyrimidine with NH-CH2-(4-pyridyl) | m.p.: 98–99° C. |

TABLE 17

| Compound No. | Structural Formula | Physical properties |
|---|---|---|
| 145 | SMe, COOBu(n), pyrazolo[1,5-a]pyrimidine with NH-(3-cyanophenyl) | m.p.: 102–103° C. |
| 146 | SMe, COOCH2Ph, pyrazolo[1,5-a]pyrimidine with Cl | m.p.: 52–54° C. |

TABLE 17-continued
| Compound No. | Structural Formula | Physical properties |
| --- | --- | --- |
| 147 | 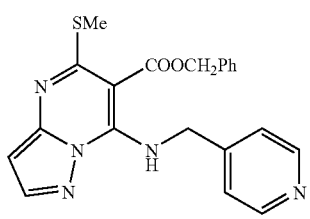 | m.p.: 122–123° C. |
| 148 | 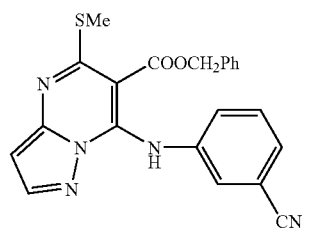 | m.p.: 141–142° C. |
| 149 | 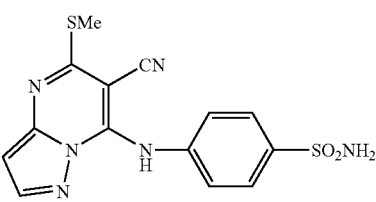 | m.p.: 285–288° C. (decomposition) |
| 150 | 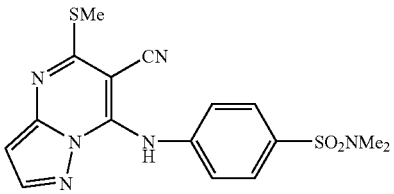 | m.p.: 303–306° C. (decomposition) |
| 151 | 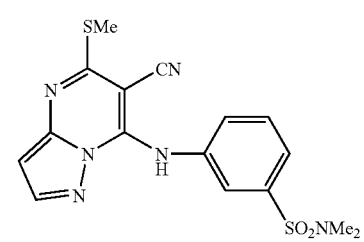 | m.p.: 205–208° C. |
| 152 | 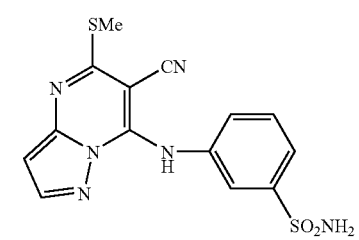 | m.p.: >280° C. |

TABLE 17-continued

| Compound No. | Structural Formula | Physical properties |
|---|---|---|
| 153 | (pyrazolo[1,5-a]pyrimidine with OMe, CN, NH-CH2-4-pyridyl) | m.p.: 193–195° C. |

TABLE 18

| Compound No. | Structural Formula | Physical properties |
|---|---|---|
| 154 | (SMe, NO2, OH) | Solid |
| 155 | (SMe, COOMe, OH) | m.p.: 192–194° C. |
| 156 | (SMe, COOPr(n), OH) | m.p.: 139–142° C. |
| 157 | (SMe, COOPr(i), OH) | m.p.: 123–125° C. |
| 158 | (SMe, COOBu(n), OH) | m.p.: 128–130° C. |
| 159 | (SMe, COOCH2Ph, OH) | Oily matter |
| 160 | (SMe, CN, 4-methylpiperidin-1-yl) | m.p.: 118–120° C. |
| 161 | (SMe, CN, NH-4-chlorophenyl) | m.p.: 275–276° C. |
| 162 | (SMe, CN, NH-3-chlorophenyl) | m.p.: 161–162° C. |

TABLE 19

| Compound No. | Structural Formula | Physical properties |
| --- | --- | --- |
| 163 | SMe, CN, NH-(2-Cl-C6H4), pyrazolo[1,5-a]pyrimidine | m.p.: 201–202° C. |
| 164 | SMe, CN, NH-(4-Me-C6H4), pyrazolo[1,5-a]pyrimidine | m.p.: 201–202° C. |
| 165 | SMe, CN, NH-indanyl, pyrazolo[1,5-a]pyrimidine | m.p.: 146–148° C. |
| 166 | SMe, CN, NH-benzothiazolyl, pyrazolo[1,5-a]pyrimidine | m.p.: 140–141° C. |
| 167 | SMe, CN, NH-(4-OCF3-C6H4), pyrazolo[1,5-a]pyrimidine | m.p.: 243–244° C. |
| 168 | SMe, CN, NH-(4-CN-C6H4), pyrazolo[1,5-a]pyrimidine | m.p.: 280–281° C. |
| 169 | SMe, CN, NH-(4-OMe-C6H4), pyrazolo[1,5-a]pyrimidine | m.p.: 214–215° C. |

TABLE 19-continued

| Compound No. | Structural Formula | Physical properties |
|---|---|---|
| 170 | SMe, CN, NH-C6H4-OH (pyrazolo[1,5-a]pyrimidine core) | m.p.: 250–256° C. |
| 171 | SMe, CN, NH-C6H4-COOMe (pyrazolo[1,5-a]pyrimidine core) | m.p.: 205–206° C. |

TABLE 20

| Compound No. | Structural Formula | Physical properties |
|---|---|---|
| 172 | SMe, CN, NH-O-CH2-C6H5 (pyrazolo[1,5-a]pyrimidine core) | m.p.: 177–178° C. |
| 173 | SMe, CN, NH-OBu(t) (pyrazolo[1,5-a]pyrimidine core) | m.p.: 167–169° C. |
| 174 | SMe, CN, NH-OCH2CH=CH2 (pyrazolo[1,5-a]pyrimidine core) | m.p.: 129–130° C. |
| 175 | SMe, CN, NH-C6H4-COOEt (pyrazolo[1,5-a]pyrimidine core) | m.p.: 191–192° C. |
| 176 | SMe, CN, NH-C6H4-COOH (pyrazolo[1,5-a]pyrimidine core) | m.p. >250° C. |
| 177 | SMe, CN, NH-(3-methylisothiazol-5-yl) (pyrazolo[1,5-a]pyrimidine core) | m.p.: 175–176° C. |
| 178 | SMe, CN, NH-(pyridin-3-yl) (pyrazolo[1,5-a]pyrimidine core) | m.p.: 214–215° C. |

TABLE 20-continued
| Compound No. | Structural Formula | Physical properties |
|---|---|---|
| 179 | 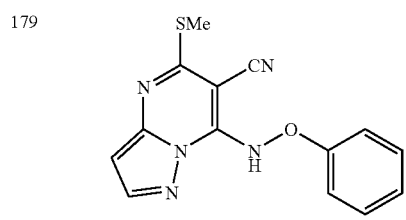 | m.p. >250° C. |
TABLE 20-continued
| Compound No. | Structural Formula | Physical properties |
|---|---|---|
| 180 | 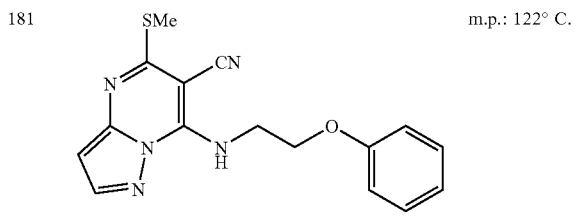 | m.p.: 142° C. |
TABLE 21
| Compound No. | Structural Formula | Physical properties |
|---|---|---|
| 181 | 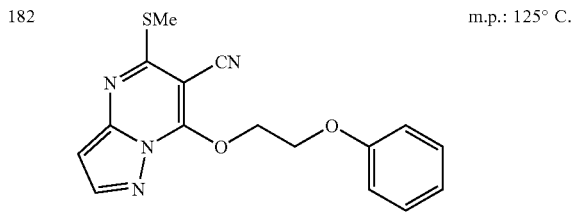 | m.p.: 122° C. |
| 182 | 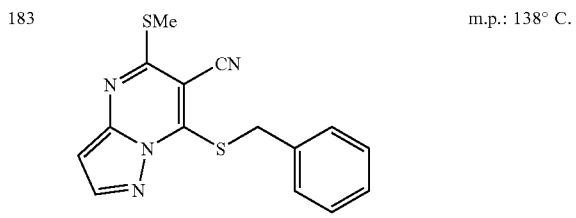 | m.p.: 125° C. |
| 183 | 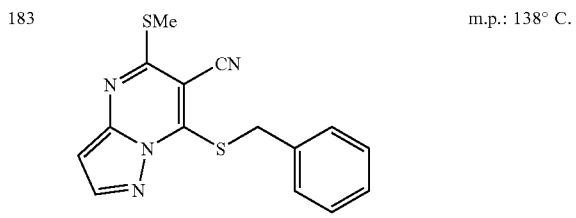 | m.p.: 138° C. |
| 184 | 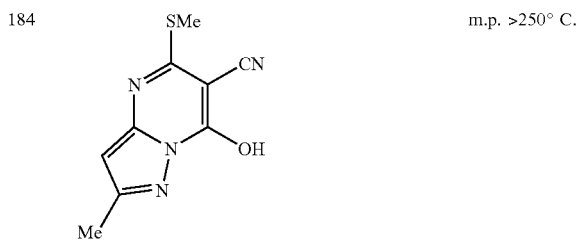 | m.p. >250° C. |

TABLE 21-continued

| Compound No. | Structural Formula | Physical properties |
|---|---|---|
| 185 | | m.p.: 182–187° C. |
| 186 | | m.p.: 235–238° C. |
| 187 | | m.p.: 204–205° C. |
| 188 | | m.p.: 190–191° C. |
| 189 | | m.p.: 185–187° C. |

TABLE 22

| Compound No. | Structural Formula | Physical properties |
|---|---|---|
| 190 | (structure: pyrazolo[1,5-a]pyrimidine with SMe, CN, NH-O-CH2-phenyl, Me) | m.p.: 155–156° C. |
| 191 | (structure: pyrazolo[1,5-a]pyrimidine with SMe, CN, NH-(3-Me-phenyl), Me) | m.p.: 174–176° C. |
| 192 | (structure: pyrazolo[1,5-a]pyrimidine with SMe, CN, NH-(3-OMe-phenyl), Me) | m.p. 142–143° C. |
| 193 | (structure: pyrazolo[1,5-a]pyrimidine with SMe, CN, NH-(4-NHCOMe-phenyl)) | m.p. >280° C. |
| 194 | (structure: pyrazolo[1,5-a]pyrimidine with SMe, CN, NH-(3-COOMe-phenyl)) | m.p.: 153–155° C. |
| 195 | (structure: pyrazolo[1,5-a]pyrimidine with SMe, CN, NH-(3-COOH-phenyl)) | m.p.: 168–171° C. |

TABLE 22-continued
| Compound No. | Structural Formula | Physical properties |
|---|---|---|
| 196 | 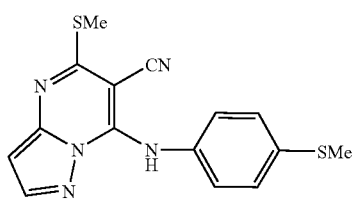 | m.p.: 190–191° C. |
| 197 | 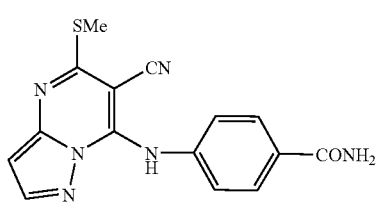 | m.p. >280° C. |
| 198 | 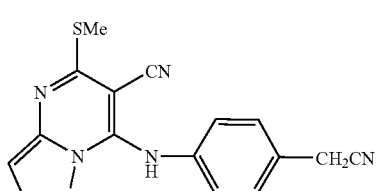 | m.p.: 268–269° C. |
TABLE 23
| Compound No. | Structural Formula | Physical properties |
|---|---|---|
| 199 | 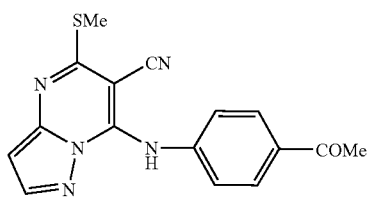 | m.p.: 260–261° C. |
| 200 | 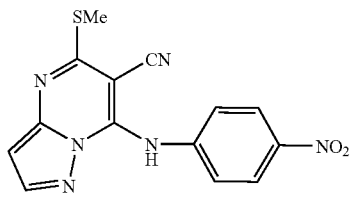 | m.p. >270° C. |
| 201 | 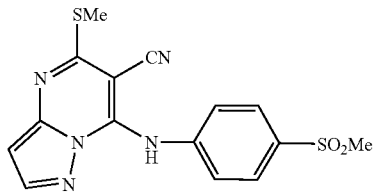 | m.p.: 241–244° C. |

TABLE 23-continued

| Compound No. | Structural Formula | Physical properties |
|---|---|---|
| 202 | (SMe, CN, pyrazolopyrimidine, NH-C6H4-NMe2) | m.p.: 250–252° C. |
| 203 | (SMe, CN, pyrazolopyrimidine, NH-C6H4-Me (ortho)) | m.p.: 192–194° C. |
| 204 | (SMe, CN, pyrazolopyrimidine, NH-O-(3-Cl-5-CF3-pyridin-2-yl)) | m.p.: 182–183° C. |
| 205 | (SMe, CN, pyrazolopyrimidine, NH-OH) | m.p.: 214–218° C. |
| 206 | (SMe, CN, pyrazolopyrimidine, NH-CH2CH2-(pyridin-2-yl)) | m.p.: 138–139° C. |
| 207 | (SMe, CN, pyrazolopyrimidine, NH-CH2-(3-Cl-5-CF3-pyridin-2-yl)) | m.p.: 185–187° C. |

TABLE 24

| Compound No. | Structural Formula | Physical properties |
| --- | --- | --- |
| 208 | | m.p.: 152–153° C. |
| 209 | | m.p.: 161–161° C. |
| 210 | | m.p.: 96–97° C. |
| 211 | | m.p.: 158–159° C. |
| 212 | | m.p.: 116–120° C. |
| 213 | | m.p.: 143–144° C. |
| 214 | | m.p.: 206–208° C. |

TABLE 24-continued

| Compound No. | Structural Formula | Physical properties |
| --- | --- | --- |
| 215 | (SMe, CN, pyrazolo[1,5-a]pyrimidine with NH-CH2CH2-(4-pyridyl)) | m.p.: 184–185° C. |
| 216 | (SMe, CN, pyrazolo[1,5-a]pyrimidine with NH-CH2CH2-(1,3-dioxane-2-yl)) | m.p.: 103–104° C. |

TABLE 25

| Compound No. | Structural Formula | Physical properties |
| --- | --- | --- |
| 217 | (SMe, CN, pyrazolo[1,5-a]pyrimidine with NH-O-CH2CH2-(1,3-dioxane-2-yl)) | m.p.: 193–195° C. |
| 218 | (SMe, CN, pyrazolo[1,5-a]pyrimidine with NH-(3-nitrophenyl)) | m.p.: 180–182° C. |
| 219 | (SMe, COOEt, pyrazolo[1,5-a]pyrimidine with OH) | Solid |
| 220 | (SMe, COOEt, pyrazolo[1,5-a]pyrimidine with Cl) | Solid |

TABLE 25-continued

| Compound No. | Structural Formula | Physical properties |
|---|---|---|
| 221 | SMe, COOEt, pyrazolopyrimidine-NH-CH2-(4-pyridyl) | m.p.: 123° C. |
| 222 | SMe, COOEt, pyrazolopyrimidine-NH-CH2-phenyl | m.p.: 114–115° C. |
| 223 | SMe, COOEt, pyrazolopyrimidine-NH-(3-cyanophenyl) | m.p.: 156–157° C. |
| 224 | SMe, COOEt, pyrazolopyrimidine-NH-(4-cyanophenyl) | m.p.: 178° C. |
| 225 | SMe, COOEt, pyrazolopyrimidine-NH-(3-nitrophenyl) | m.p.: 166–168° C. |

TABLE 26

| Compound No. | Structural Formula | Physical properties |
|---|---|---|
| 226 | SMe, COOEt, pyrazolopyrimidine-NH-(4-nitrophenyl) | m.p.: 170° C. |

TABLE 26-continued

| Compound No. | Structural Formula | Physical properties |
|---|---|---|
| 227 | SMe, CONHPr(i), pyrazolopyrimidine with NH-CH2-(4-pyridyl) | m.p.: 106–108° C. |
| 228 | SMe, CN, pyrazolopyrimidine with N(Et)-CH2-(4-pyridyl) | m.p.: 102–103° C. |
| 229 | SMe, CN, pyrazolopyrimidine with OMe | m.p.: 223–224° C. |

Test Example 1

Pharmacological Test

Glucose Uptake Test by L6 Cells

Each of compounds under test was applied to L6 cells (rat cells originally derived from skeletal muscles) by the following method to measure the stimulating effect on glucose uptake. Namely, L6 cells were suspended in α-minimum essential medium (hereinafter referred to simply as MEM) containing 10% fetal bovine serum (hereinafter referred to simply as FBS), and inoculated into a 96-well plastic plate in an amount of $5 \times 10^4$ cells/well and cultivated in an incubator (5% carbon dioxide gas, 37° C.) until the cells grew all over the well. Then, the culture medium was switched to MEM solution containing 2% BS, followed by cultivation further for from 7 to 10 ays (the culture medium was exchanged every three days) to differentiate the cells into skeletal muscle cells. Then, the culture medium was replaced with MEM solution without FBS, followed by cultivation for three hours, and then the compound under test prepared to a treatment concentration (diluted with MEM solution without FBS) was reacted with the skeletal muscle cells at 37° C. for 1 hour. The cells were washed with Krebs-Henseleit-Ringer buffer solution (hereinafter referred to simply as KHR buffer solution), and 2-deoxy-[$^3$H]-glucose was added to the cells in the KHR buffer solution, followed by treatment at 37° C. for 10 minutes. The treatment solution was removed, the cells were washed with the KHR buffer solution, then the cells were dissolved in a 1N sodium hydroxide solution in an appropriate amount, and the [$^3$H] radio activity was measured by means of a liquid scintillation counter (cpm) The percentage of the glucose uptake was represented by the percentage of radio activity when the compound under test was applied, taking the radio activity of the control (the MEM solvent alone was applied) as 100%. Each of the compounds as identified in Table 27 was used for treatment at a concentration of each of 10 μg/ml and 100 μg/ml to examine the stimulating effect on glucose uptake. As a result, it was confirmed that all the tested compounds showed stimulating effects on glucose uptake of at least 115% at least within a range of from 10 μg/ml to 100 μg/ml.

TABLE 27

| Treatment concentration (μg/ml) | Compound No. | Ratio activity (%) |
|---|---|---|
| 10 | 2, 3, 9, 11, 22, 40, 43, 50, 60, 64, 68, 71, 72, 74, 79, 80, 82, 105, 112, 118, 120, 121, 122, 126, 131, 133, 135, 136, 138, 144, 161, 163, 164, 168, 172, 178, 186, 191, 200, 203, 205, 206, 210, 211, 215, 218, 221, 222, 223, 224, 225, 226 | >115 |
| 100 | 2, 3, 4, 5, 8, 9, 14, 15, 17, 22, 25 27, 28, 29, 40, 43, 46, 47, 48, 50, 53, 68, 71, 83, 108, 118, 121, 122, 130, 131, 132, 135, 136, 144, 168, 172, 174, 177, 178, 186, 190, 200, 210, 211, 218, 221, 223, 226 | >115 |

Test Example 2

Beneficial Effect Test

Test for Hypoglycemic Effect

Using KK-Ay/Ta mice (purchased from CLEA Japan, Inc.) as spontaneous diabetic type II, the hypoglycemic effect of each of compounds under test was confirmed by the following method.

Male KK-Ay/Ta mice sufficiently preliminarily bred and acclimatized were classified into groups, each consisting of six mice, and each of the compounds under test was administered. Each of the compounds under test as suspended in 0.5% carboxymethyl cellulose (manufactured by Nacalai Tesque), and each compound was orally administered singly in a dose of 50 mg/kg (10 ml/kg) by means of an oral conductor. At the same time, as a group of vehicle control, 0.5% carboxymethyl cellulose was administered in the same volume (10 ml/kg) as for the group of administration of compound under test.

Collection of blood was carried out by the following method before the administration of each of the compounds under test or the vehicle, and at the time as identified in Table 28 after the administration. The tail vein of each mouse was shallowly cut by the edge of a razor to cause bleeding in an amount of blood of from 10 to 20 µL, and the blood was collected by a micropipet. The collected blood samples were immediately mixed with a heparin solution (20 U/ml) (manufactured by Mochida Yakuhin) in the same amount as the respective collected blood samples, and subjected to centrifugation at 4° C. for 5 minutes (10,000 rpm) by means of a cooling centrifugal machine. The plasma after the centrifugation was obtained as a sample for blood glucose level measurement.

The blood glucose level was measured by means of glucose oxidase method, and measured by using a commercially available assay kit (Glucose CII TEST WAKO, manufactured by Wako Pure Chemical Industries, Ltd.). Measurement was carried out on the day after the collection of blood, and the obtained plasma was stored at −20° C. before the measurement.

The blood glucose level at the time of collection of blood was calculated as the percentage to the blood glucose level before administration of the compound under test, and the hypoglycemic effect of the compound under test was evaluated by comparison with the change of the blood glucose level (percentage) of the group of vehicle control at the time of collection of blood. The results are shown in Table 28. The evaluation results of the hypoglycemic effect are considered to have a significant difference compared with the vehicle control by means of Wilcoxon's rank sum test ($P \leq 0.05$)

TABLE 28

| Compound under test | Time for collection of blood | Rate of change of blood glucose level | Rate of change of blood glucose level of vehicle control |
| --- | --- | --- | --- |
| Compd. No. 3 | After 3 hours | 78% | 93% |
| Compd. No. 8 | After 6 hours | 68% | 88% |
| Compd. No. 50 | After 3 hours | 74% | 96% |
| Compd. No. 186 | After 3 hours | 80% | 96% |
| Compd. No. 200 | After 3 hours | 79% | 96% |

Industrial Applicability

The preventive or therapeutic medicines for diabetes of the present invention show stimulating effect on glucose uptake by application to skeletal muscle cells only for a short time, and accordingly they are useful as preventive or therapeutic medicines particularly for diabetes; impaired glucose tolerance; various diabetic complications such as hyperlipidemia, vascular diseases, retinopathy, nephropathy, neuropathy and hypertension; and obesity.

What is claimed is:
1. A fused-heterocyclic compound of the formula (I') or its salt:

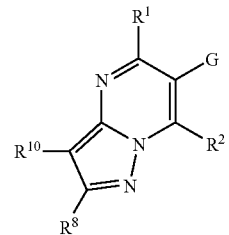

wherein G is CN, $NO_2$, $CO_2R^4$
  wherein $R^4$ is a hydrogen atom, an alkenyl group which may be substituted, an alkynyl group which may be substituted, a cycloalkyl group which may be substituted, a cycloalkenyl group which may be substituted, an aryl group which may be substituted or a heterocyclic group which may be substituted,
$SO_2NR^aR^b$
  wherein each of $R^a$ and $R^b$ which are independent of each other, is a hydrogen atom, a hydroxyl group, an alkoxy group, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted, or $R^a$ and $R^b$ together form a ring or
$CONR^aR^b$, wherein $R^a$ and $R^b$ are as defined above;
$R^1$ is a halogen atom, a —O—$R^5$ group
  wherein $R^5$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted,
or a —S—$R^5$ group wherein $R^5$ is as defined above;
$R^2$ is a halogen atom, a —O—$R^5$ group, wherein $R^5$ as defined above, or an amino group which may be substituted; and
each of $R^8$ and $R^{10}$ which are independent of each other, is a hydrogen atom, a halogen atom or an alkyl group; wherein the compound wherein G is CN, $R^1$ is —SMe, $R^2$ is $NH_2$, $R^8$ is Me, and $R^{10}$ is hydrogen is excluded.

2. The compound or its salt according to claim 1, wherein $R^2$ is an amino group which may be substituted.

3. The compound or its salt according to claim 1, wherein $R^2$ is an amino group which may be substituted, and each of $R^8$ and $R^{10}$ is a hydrogen atom.

4. The compound or its salt according to claim 3, wherein the amino group which may be substituted represented by $R^2$ is a —$NR^cR^d$ group,
  wherein each of $R^c$ and $R^d$ which are independent of each other, is a hydrogen atom, a —O—$R^5$ group
    wherein $R^5$ is a hydrogen atom, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted,
an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted, or $R^c$ and $R^d$ together form a ring.

5. The compound or its salt according to claim 1, wherein G is CN, $CO_2R^4$
   wherein $R^4$ is a hydrogen atom, an alkenyl group which may be substituted, an alkynyl group which may be substituted, a cycloalkyl group which may be substituted, a cycloalkenyl group which may be substituted, an aryl group which may be substituted or a heterocyclic group which may be substituted, $SO_2NR^aR^b$
   wherein each of $R^a$ and $R^b$ which are independent of each other, is a hydrogen atom, a hydroxyl group, an alkoxy group, an alkyl group which may be substituted, an alkenyl group which may be substituted, an alkynyl group which may be substituted, a cycloalkyl group which may be substituted, a cycloalkenyl group which may be substituted or a heterocyclic group which may be substituted, or $R^a$ and $R^b$ together form a ring,
or $CONR^{a'}R^{b'}$
   wherein each of $R^{a'}$ and $R^{b'}$ which are independent of each other, is a hydroxyl group, an alkoxy group, an alkyl group which may be substituted, an alkenyl group which may be substituted, an alkynyl group which may be substituted, a cycloalkyl group which may be substituted, a cycloalkenyl group which may be substituted, an aryl group which may be substituted or a heterocyclic group which may be substituted, or $R^{a'}$ and $R^{b'}$ together may form a ring.

6. A pharmaceutical composition which contains the compound or its salt as defined in claim 1 as an active ingredient and a pharmaceutically acceptable carrier.

7. A method for treating diabetes in a patient in need thereof, comprising administering a compound of claim 1 in an amount sufficient to treat diabetes in the patient.

8. A method for stimulating glucose uptake in skeletal muscle cells in a patient thereof, comprising administering a compound of claim 1 in an amount sufficient to stimulate glucose uptake in skeletal muscle cells in the patient.

9. A method for treating impaired glucose tolerance in a patient in need thereof, comprising administering a compound of claim 1 in an amount sufficient to treat impaired glucose tolerance in the patient.

10. A method for treating at least one diabetic complication selected for the group consisting of hyperlipidemia, vascular diseases, retinopathy, nephropathy, neuropathy and hypertension in a patient in need thereof, comprising administering a compound of claim 1 in an amount sufficient to treat the at least one diabetic complication in the patient.

* * * * *

UNITED STATES PATENT AND TRADEMARK OFFICE
CERTIFICATE OF CORRECTION

| | | |
|---|---|---|
| PATENT NO. | : 7,067,520 B2 | |
| APPLICATION NO. | : 10/416164 | |
| DATED | : June 27, 2006 | |
| INVENTOR(S) | : Kato et al. | |

It is certified that error appears in the above-identified patent and that said Letters Patent is hereby corrected as shown below:

On the title page, Item (30), the Foreign Application Priority Data information is incorrect. Item (30) should read:

-- (30) Foreign Application Priority Data

Nov. 17, 2000   (JP) …………………… 2000-351764 --

Signed and Sealed this

Twelfth Day of September, 2006

JON W. DUDAS
*Director of the United States Patent and Trademark Office*